US011744927B2

(12) United States Patent
Falo, Jr. et al.

(10) Patent No.: US 11,744,927 B2
(45) Date of Patent: Sep. 5, 2023

(54) DISSOLVABLE MICRONEEDLE ARRAYS FOR TRANSDERMAL DELIVERY TO HUMAN SKIN

(71) Applicants: University of Pittsburgh—Of the Commonwealth System of Higher Education, Pittsburgh, PA (US); Carnegie Mellon University, Pittsburgh, PA (US)

(72) Inventors: Louis D. Falo, Jr., Wexford, PA (US); Geza Erdos, Wexford, PA (US); O. Burak Ozdoganlar, Sewickley, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 16/861,112

(22) Filed: Apr. 28, 2020

(65) Prior Publication Data
US 2020/0397955 A1    Dec. 24, 2020

Related U.S. Application Data

(60) Continuation of application No. 14/458,050, filed on Aug. 12, 2014, now abandoned, which is a division of
(Continued)

(51) Int. Cl.
*A61M 37/00* (2006.01)
*A61L 31/14* (2006.01)
(Continued)

(52) U.S. Cl.
CPC ............ *A61L 31/148* (2013.01); *A61L 31/042* (2013.01); *A61L 31/06* (2013.01); *A61L 31/16* (2013.01);
(Continued)

(58) Field of Classification Search
None
See application file for complete search history.

(56) References Cited

U.S. PATENT DOCUMENTS

| 5,312,456 A | 5/1994 | Reed |
| 5,658,515 A | 8/1997 | Lee et al. |

(Continued)

FOREIGN PATENT DOCUMENTS

| CN | 147590 A | 3/2004 |
| CN | 1621102 | 6/2005 |

(Continued)

OTHER PUBLICATIONS

Filiz S., Xie L., Weiss L.E., Ozdoganlar O.B.,: Micromilling of Microbarbs for Medical Implants. Int J Mach Tools Manuf. 2008; 48 (3-4): p. 459-472 (Year: 2008).*

(Continued)

*Primary Examiner* — Mohammad M Ameen
(74) *Attorney, Agent, or Firm* — Klarquist Sparkman, LLP

(57) ABSTRACT

A method of forming a microneedle array can include forming a sheet of material having a plurality of layers and micromilling the sheet of material to form a microneedle array. At least one of the plurality of layers can include a bioactive component, and the microneedle array can include a base portion and plurality of microneedles extending from the base portion.

13 Claims, 17 Drawing Sheets

Related U.S. Application Data application No. 12/910,516, filed on Oct. 22, 2010, now Pat. No. 8,834,423.

(60) Provisional application No. 61/279,623, filed on Oct. 23, 2009.

(51) Int. Cl.
- A61L 31/04 (2006.01)
- A61L 31/06 (2006.01)
- A61L 31/16 (2006.01)
- B23C 3/00 (2006.01)

(52) U.S. Cl.
CPC ............ *A61M 37/0015* (2013.01); *B23C 3/00* (2013.01); *A61L 2300/426* (2013.01); *A61L 2300/604* (2013.01); *A61L 2400/06* (2013.01); *A61M 2037/0053* (2013.01); *B23C 2215/00* (2013.01); *B23C 2220/48* (2013.01); *B23C 2226/00* (2013.01); *Y10T 409/303752* (2015.01)

(56) References Cited

U.S. PATENT DOCUMENTS

| | | |
|---|---|---|
| 6,331,266 B1 | 12/2001 | Powell et al. |
| 6,451,240 B1 | 9/2002 | Sherman et al. |
| 6,511,463 B1 | 1/2003 | Wood et al. |
| 6,565,871 B2 | 5/2003 | Roser et al. |
| 6,611,707 B1 | 8/2003 | Prausnitz et al. |
| 6,623,707 B1 | 9/2003 | Addiego et al. |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,743,211 B1 | 6/2004 | Prausnitz et al. |
| 6,767,211 B2 | 7/2004 | Hall et al. |
| 6,881,203 B2 | 4/2005 | Delmore et al. |
| 6,899,838 B2 | 5/2005 | Lastovich |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 7,052,268 B2 | 5/2006 | Powell et al. |
| 7,132,054 B1 | 11/2006 | Kravitz et al. |
| 7,211,062 B2 | 5/2007 | Kwon |
| 7,226,439 B2 | 6/2007 | Prausnitz et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,332,197 B2 | 2/2008 | Wood et al. |
| 7,364,568 B2 | 4/2008 | Angel et al. |
| 7,416,541 B2 | 8/2008 | Yuzhakov et al. |
| 7,429,333 B2 | 9/2008 | Chiou et al. |
| 7,473,247 B2 | 1/2009 | Mikszta et al. |
| 7,497,980 B2 | 3/2009 | Xu et al. |
| 7,560,036 B2 | 7/2009 | Golubovic-Liakopoulos et al. |
| 7,578,954 B2 | 8/2009 | Gartstein et al. |
| 7,588,552 B2 | 9/2009 | Yeshurun et al. |
| 7,591,806 B2 | 9/2009 | Xu |
| 7,611,481 B2 | 11/2009 | Cleary et al. |
| 7,648,484 B2 | 1/2010 | Yeshurun et al. |
| 7,651,475 B2 | 1/2010 | Angel et al. |
| 7,658,728 B2 | 2/2010 | Yuzhakov |
| 7,699,819 B2 | 4/2010 | Yeung et al. |
| 7,731,968 B2 | 6/2010 | Mikszta et al. |
| D619,245 S | 7/2010 | Moga et al. |
| 7,753,888 B2 | 7/2010 | Mukerjee et al. |
| 7,763,203 B2 | 7/2010 | Arias et al. |
| 7,785,301 B2 | 8/2010 | Yuzhakov |
| 7,846,488 B2 | 12/2010 | Johnson et al. |
| 7,850,657 B2 | 12/2010 | Yeshurun et al. |
| D638,534 S | 5/2011 | Moga et al. |
| 7,942,827 B2 | 5/2011 | Mir et al. |
| 8,052,633 B2 | 11/2011 | Kendall |
| 8,057,842 B2 | 11/2011 | Choi et al. |
| 8,062,573 B2 | 11/2011 | Kwon |
| 8,062,835 B2 | 11/2011 | Tomono |
| 8,088,321 B2 | 1/2012 | Ferguson et al. |
| 8,101,114 B2 | 1/2012 | Park et al. |
| 8,137,736 B2 | 3/2012 | Zhu et al. |
| 8,162,901 B2 | 4/2012 | Gonnelli et al. |
| 8,167,852 B2 | 5/2012 | Quan et al. |
| 8,172,815 B2 | 5/2012 | Down et al. |
| 8,192,787 B2 | 6/2012 | Kirby |
| 8,216,190 B2 | 7/2012 | Gartstein et al. |
| 8,236,368 B2 | 8/2012 | Jung et al. |
| 8,246,582 B2 | 8/2012 | Angel et al. |
| 8,246,893 B2 | 8/2012 | Ferguson et al. |
| 8,250,729 B2 | 8/2012 | Lee et al. |
| 8,257,324 B2 | 9/2012 | Prausnitz et al. |
| 8,267,889 B2 | 9/2012 | Cantor et al. |
| 8,328,757 B2 | 12/2012 | Beebe et al. |
| 8,353,861 B2 | 1/2013 | Tobinaga et al. |
| 8,354,033 B2 | 1/2013 | Scholten et al. |
| 8,361,037 B2 | 1/2013 | Gonnelli |
| 8,366,677 B2 | 2/2013 | Kaspar et al. |
| 8,376,984 B2 | 2/2013 | James |
| 8,402,629 B2 | 3/2013 | Lee et al. |
| 8,414,548 B2 | 4/2013 | Yuzhakov |
| 8,414,959 B2 | 4/2013 | Hye-Ok et al. |
| 8,419,708 B2 | 4/2013 | Tokumoto et al. |
| 8,444,622 B2 | 5/2013 | Eckhoff et al. |
| 8,449,807 B2 | 5/2013 | Ferguson et al. |
| 8,454,844 B2 | 6/2013 | Yeshurun et al. |
| 8,491,534 B2 | 7/2013 | Takada |
| 8,506,530 B2 | 8/2013 | Laermer et al. |
| 8,506,980 B2 | 8/2013 | Takada |
| 8,540,672 B2 | 9/2013 | McAllister |
| 8,545,741 B2 | 10/2013 | Jung et al. |
| 8,551,391 B2 | 10/2013 | Chang et al. |
| 8,554,317 B2 | 10/2013 | Duan |
| 8,560,059 B2 | 10/2013 | Hoarau et al. |
| 8,579,862 B2 | 11/2013 | Kobayashi et al. |
| 8,603,384 B2 | 12/2013 | Luttge et al. |
| 8,636,696 B2 | 1/2014 | Ross et al. |
| 8,637,136 B2 | 1/2014 | Ferguson et al. |
| 8,671,544 B2 | 3/2014 | Xu et al. |
| 8,696,637 B2 | 4/2014 | Ross |
| 8,696,638 B2 | 4/2014 | Terahara et al. |
| 8,708,966 B2 | 4/2014 | Allen et al. |
| 8,734,697 B2 | 5/2014 | Chen et al. |
| 8,741,377 B2 | 6/2014 | Choi et al. |
| 8,747,362 B2 | 6/2014 | Terahara et al. |
| 8,758,298 B2 | 6/2014 | Cantor et al. |
| 8,771,781 B2 | 7/2014 | Tokumoto et al. |
| 8,784,368 B2 | 7/2014 | Eckhoff et al. |
| 8,784,373 B2 | 7/2014 | Gharib et al. |
| 8,784,383 B2 | 7/2014 | Cole et al. |
| 8,784,384 B2 | 7/2014 | Boyden et al. |
| 8,784,385 B2 | 7/2014 | Boyden et al. |
| 8,784,860 B2 | 7/2014 | Falotico et al. |
| 8,785,400 B2 | 7/2014 | Levetan et al. |
| 8,788,037 B2 | 7/2014 | Della Rocca et al. |
| 8,788,211 B2 | 7/2014 | Boyden et al. |
| 8,788,212 B2 | 7/2014 | Boyden et al. |
| 8,790,257 B2 | 7/2014 | Libbus et al. |
| 8,790,259 B2 | 7/2014 | Katra et al. |
| 8,790,658 B2 | 7/2014 | Cigarini et al. |
| 8,791,062 B2 | 7/2014 | Hsu et al. |
| 8,791,107 B2 | 7/2014 | Chang et al. |
| 8,793,075 B2 | 8/2014 | Boyden et al. |
| 8,795,174 B2 | 8/2014 | Manicka et al. |
| 8,795,201 B2 | 8/2014 | Escutia et al. |
| 8,795,230 B2 | 8/2014 | Schoonmaker et al. |
| 8,795,234 B2 | 8/2014 | Kadamus et al. |
| 8,795,259 B2 | 8/2014 | Beebe et al. |
| 8,796,436 B2 | 8/2014 | Manoharan et al. |
| 8,798,722 B2 | 8/2014 | Rylander et al. |
| 8,798,932 B2 | 8/2014 | Boyden et al. |
| 8,798,933 B2 | 8/2014 | Boyden et al. |
| 8,821,446 B2 | 9/2014 | Trautman et al. |
| 8,821,779 B2 | 9/2014 | Ferguson et al. |
| 8,834,423 B2 | 9/2014 | Falo, Jr. |
| 2002/0082543 A1* | 6/2002 | Park .......... A61N 1/30 604/21 |

(56) References Cited

U.S. PATENT DOCUMENTS

| | | |
|---|---|---|
| 2002/0193729 A1 | 12/2002 | Cormier et al. |
| 2002/0198509 A1 | 12/2002 | Mikszta et al. |
| 2004/0058882 A1 | 3/2004 | Eriksson et al. |
| 2005/0008683 A1 | 1/2005 | Mikszta et al. |
| 2005/0013221 A1 | 1/2005 | Takanobu |
| 2005/0019918 A1 | 1/2005 | Sumimoto et al. |
| 2005/0065463 A1 | 3/2005 | Tobinaga et al. |
| 2005/0089553 A1 | 4/2005 | Cormier et al. |
| 2005/0095298 A1 | 5/2005 | Gronlund et al. |
| 2007/0161964 A1 | 7/2007 | Yuzhakov |
| 2007/0260201 A1 | 11/2007 | Prausnitz et al. |
| 2007/0299388 A1 | 12/2007 | Chan et al. |
| 2008/0009763 A1* | 1/2008 | Chiou ............ A61B 5/25 600/373 |
| 2008/0208134 A1* | 8/2008 | Tomono ............ A61P 3/10 604/173 |
| 2008/0213461 A1 | 9/2008 | Gill et al. |
| 2008/0214987 A1* | 9/2008 | Xu ............ A61K 31/337 604/21 |
| 2008/0221532 A1 | 9/2008 | Ogawa |
| 2008/0269658 A1 | 10/2008 | Vinton et al. |
| 2008/0269685 A1 | 10/2008 | Singh et al. |
| 2009/0017210 A1 | 1/2009 | Andrianov et al. |
| 2009/0054842 A1 | 2/2009 | Yeshurun et al. |
| 2009/0232855 A1 | 9/2009 | Sang et al. |
| 2010/0042137 A1 | 2/2010 | Oronsky et al. |
| 2010/0228203 A1 | 9/2010 | Quan et al. |
| 2010/0233093 A1 | 9/2010 | Oh et al. |
| 2011/0046575 A1 | 2/2011 | Takada |
| 2011/0098651 A1 | 4/2011 | Falo, Jr. |
| 2011/0172605 A1 | 7/2011 | Berenschot et al. |
| 2011/0230736 A1 | 9/2011 | Tepper et al. |
| 2012/0064124 A1 | 3/2012 | McClain et al. |
| 2012/0078189 A1 | 3/2012 | Ogawa et al. |
| 2012/0123341 A1 | 5/2012 | Birchall et al. |
| 2012/0265145 A1 | 10/2012 | Mefti et al. |
| 2013/0072902 A1 | 3/2013 | Takada et al. |
| 2013/0096532 A1 | 4/2013 | Ozel et al. |
| 2013/0165772 A1 | 6/2013 | Traverso et al. |
| 2013/0190794 A1 | 7/2013 | Kendall et al. |
| 2013/0338632 A1 | 12/2013 | Kaplan et al. |
| 2014/0066843 A1 | 3/2014 | Zhang et al. |
| 2014/0142492 A1 | 5/2014 | Jung et al. |
| 2014/0142541 A1 | 5/2014 | Yan et al. |
| 2014/0200511 A1 | 7/2014 | Boyden et al. |
| 2015/0030642 A1 | 1/2015 | Wu et al. |
| 2015/0126923 A1 | 5/2015 | Falo, Jr. |
| 2016/0158512 A1 | 6/2016 | Tamaru et al. |
| 2018/0272621 A1 | 9/2018 | Falo, Jr. et al. |
| 2018/0304062 A1 | 10/2018 | Falo, Jr. et al. |
| 2018/0333898 A1 | 11/2018 | Francis et al. |
| 2019/0000966 A1 | 1/2019 | Falo, Jr. et al. |
| 2019/0255307 A1 | 8/2019 | Falo, Jr. et al. |

FOREIGN PATENT DOCUMENTS

| | | |
|---|---|---|
| JP | 2005-35945 | 2/2005 |
| JP | 2010-069253 A | 4/2010 |
| JP | 2011-224332 | 11/2011 |
| WO | WO 98/00194 | 1/1998 |
| WO | WO 98/29134 | 7/1998 |
| WO | WO 2005/025413 | 9/2005 |
| WO | WO 2007/080596 A2 | 7/2007 |
| WO | WO 2007/113648 A2 | 10/2007 |
| WO | WO 2008/091602 | 7/2008 |
| WO | WO 2008/114218 A2 | 9/2008 |
| WO | WO 2009-004995 | 1/2009 |
| WO | WO 2009/009004 | 1/2009 |
| WO | WO 2009/040548 | 4/2009 |
| WO | WO 2009/081122 | 7/2009 |
| WO | WO 2009/094394 | 7/2009 |
| WO | WO 2010/022252 | 2/2010 |
| WO | WO 2010/071918 | 7/2010 |
| WO | WO 2010/141377 | 12/2010 |
| WO | WO 2011/135531 | 11/2011 |
| WO | WO 2011/135532 A2 | 11/2011 |
| WO | WO 2011/135533 A2 | 11/2011 |
| WO | WO 2012/020332 A2 | 2/2012 |
| WO | WO 2012/054582 | 4/2012 |
| WO | WO 2012/153266 | 11/2012 |
| WO | WO 2013/033400 | 3/2013 |
| WO | WO 2013/166162 | 11/2013 |
| WO | WO 2014/012147 | 1/2014 |

OTHER PUBLICATIONS

Lee J.W., Park J-H, Prausnitz M. R., Dissolving Microneedles for Transdermal Drug Delivery, Biomaterials, May 2008; 29 (13): p. 2113-2124 (Year: 2008).*

Park et al. "Polymer Microneedles for Controlled-Release Drug Delivery": Pharmaceutical Research, vol. 23, No. 5 May 2006 (Year: 2006).*

Cobleigh et al., "A phase II study of Adriamycin in previously untreated squamous cell carcinoma of the head and neck," *Cancer* 56(11): 2573-2575, 1985.

European Search Report dated Mar. 10, 2016 by the European Patent Office, for EPC App. No. 13784192.0, 14 pages.

Examination Report, dated Dec. 16, 2016, for corresponding Australian Patent Application No. 2013256348, 3 pages.

Filiz et al., "Micromilling of microbarbs for medical implants," *International Journal of Machine Tools and Manufacture* 48(3-4): 459-472, 2008.

International Preliminary Report on Patentability dated Sep. 16, 2013 by the Korean Intellectual Property Office, acting as ISA for PCT application No. PCT/US2013/039084, 8 pages.

International Preliminary Report on Patentability dated Jan. 14, 2016 by the Australian Patent Office, acting as ISA for PCT application No. PCT/US2015/059556, 6 pages.

International Preliminary Report on Patentability dated Jul. 5, 2016 by the Korean Intellectual Property Office, acting as ISA for PCT application No. PCT/US2016/02374, 15 pages.

International Search Report and Written Opinion dated Sep. 16, 2013 by the Korean Intellectual Property Office, acting as ISA for PCT application No. PCT/US2013/039084, 10 pages.

International Search Report and Written Opinion dated Jan. 14, 2016 by the Australian Patent Office, acting as ISA for PCT App. No. PCT/US2015/059556, 11 pages.

International Search Report and Written Opinion dated Jul. 5, 2016 by the Korean Intellectual Property Office, acting as ISA for PCT application No. PCT/US2016/02374, 18 pages.

Kim et al., "Microneedles for drug and vaccine delivery," *Advanced Drug Delivery Reviews* 64(14): 1574-1568, 2012.

Khodadust et al., "Development of poly (I: C) modified doxorubicin loaded magnetic dendrimer nanoparticles for targeted combination therapy," *Biomedicine & Pharmacotherapy* 68(8): 979-987, 2014.

Lee et al., "Dissolving microneedles for transdermal drug delivery." *Biomaterials* 29(13): 2113-2124, 2008.

Lee et al., "Transdermal drug delivery system using microneedles," Korean Journal of Skin Barrier Research 15(1): 22-33, Jun. 2013 (with English-language machine translation).

Ma et al., "Poly (I: C) inhibits melanoma metastasis and enhances chemerin expression and NK cell recruitment via a RIG-like helicase innate immune/MAVS-dependent mechanism," In C38. Pulmonary and Systemic Inflammation, American Thoracic Society, pp. A4165-A4165, 2013.

Office Action, dated Jan. 25, 2017, for corresponding Japanese Patent Application No. 2015-510434, with English language translation, 11 pages.

Office Action, dated Apr. 14, 2017, in corresponding Chinese Patent Application No. 201380031604.6, with English-language translation, 9 pages.

Office Action, dated Sep. 14, 2017, for corresponding Japanese Patent Application No. 2015-510434, with English language translation, 11 pages.

Office Action, dated Sep. 26, 2017, for corresponding Mexican Patent Application No. MX/a/2014/013234, no English language translation, 4 pages.

(56) References Cited

OTHER PUBLICATIONS

Office Action, dated Oct. 31, 2017, in corresponding Chinese Patent Application No. 201380031604.6, with English-language translation, 18 pages.
Office Action, dated Dec. 27, 2017, for corresponding Taiwanese Application No. 2017-78229, no English language translation, 5 pages.
Shiozuka et al., "Transdermal delivery of adriamycin to transplanted Ehrlich ascites tumor in mice," *Pharmaceutics* 5(3): 385-391, 2013.
Von Boehmer et al., "Therapeutic opportunities for manipulating T Reg cells in autoimmunity and cancer," *Nature Reviews Drug discovery* 12(1): 51-63, Jan. 2013.
Xie et al., "Toll-like receptor 2 mediates invasion via activating NF-κB in MDA-MB-231 breast cancer cells," *Biochemical and Biophysical Research Communications* 379(4): 1027-1032, 2009.
Bandyopadhyay et al. "Skin codelivery of contact sensitizers and neurokinin-1 receptor antagonists integrated in microneedle arrays suppresses allergic contact dermatitis," *Journal of Allergy and Clinical Immunology* pp. 114-130, Jan. 2022.

* cited by examiner

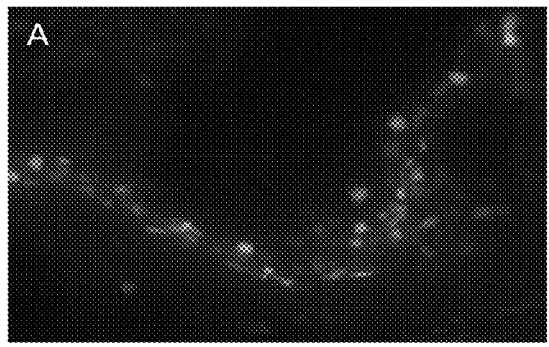 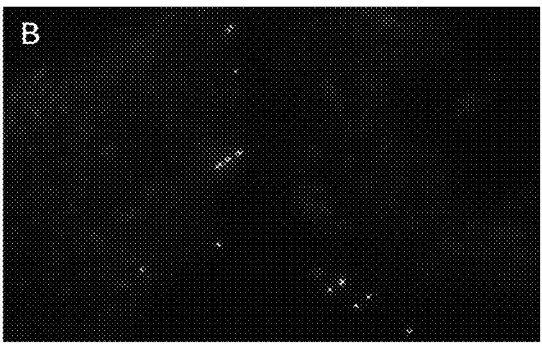
FIG. 19A    FIG. 19B
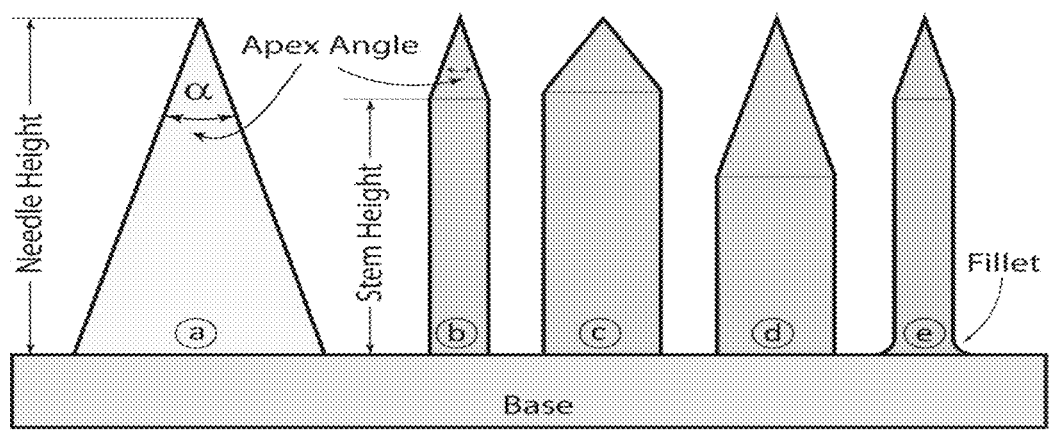
FIG. 20

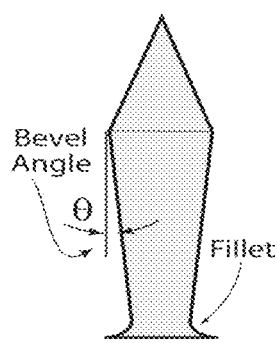
FIG. 21
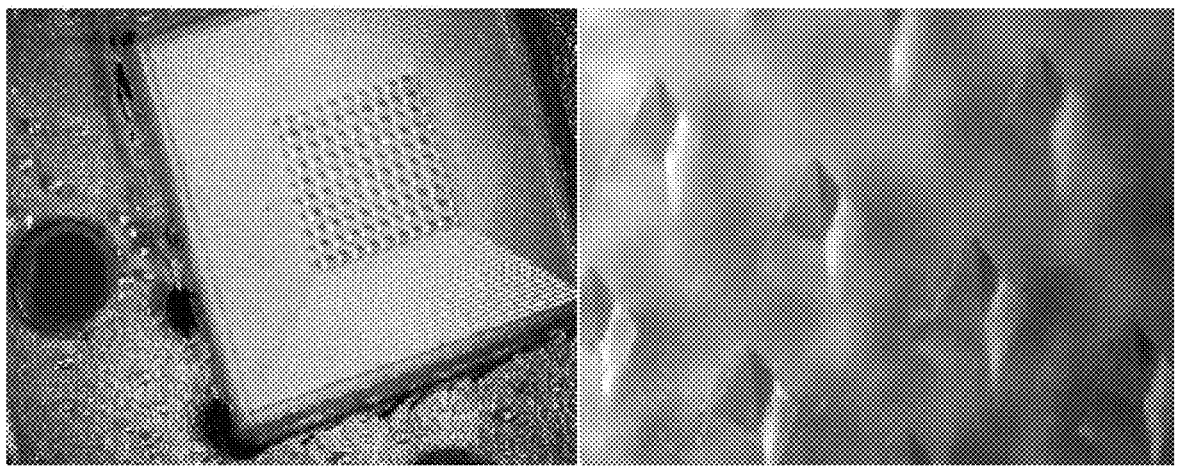
FIG. 22
FIG. 23

Table 4.2.5 Transfer of $^3$H-labeled CMC-microneedle material into human skin explants by pyramidal and pillar-type needles.

| Array Batches | Pyramid Needles (cpm/patch) | STDev (%) | Pyramidal Needles OVA Transferred (µg/patch) | Pillar-Type Needles (cpm/patch) | STDev (%) | Pillar-Type Needles OVA Transferred (µg/patch) | Pillar to Pyramid Ratio |
|---|---|---|---|---|---|---|---|
| Batch A | 2459.00 | 17.56 | 1.70 | 11700.50 | 31.52 | 8.08 | 4.76 |
| Batch B | 3273.50 | 57.39 | 2.26 | 12816.50 | 21.45 | 8.85 | 3.92 |
| Batch C | 2757.75 | 46.13 | 1.90 | 12240.00 | 26.77 | 8.46 | 4.44 |
| Batch D | 3782.00 | 36.27 | 2.61 | 10921.50 | 9.32 | 7.55 | 2.89 |
| IntraBatch AVG | 3068.06 | 19.00 | 2.12 | 11919.63 | 6.77 | 8.24 | 3.89 |

FIG. 26

DISSOLVABLE MICRONEEDLE ARRAYS FOR TRANSDERMAL DELIVERY TO HUMAN SKIN

CROSS REFERENCE TO RELATED APPLICATIONS

This application is a continuation of U.S. patent application Ser. No. 14/458,050, filed Aug. 12, 2014, which is a divisional of U.S. application Ser. No. 12/910,516, filed Oct. 22, 2010, now U.S. Pat. No. 8,834,423, which claims the benefit of U.S. Provisional Application No. 61/279,623, which was filed on Oct. 23, 2009. The prior applications are incorporated by reference herein in their entirety.

ACKNOWLEDGMENT OF GOVERNMENT SUPPORT

This invention was made with government support under AI006008 and AI076060 awarded by the National Institutes of Health. The government has certain rights in the invention.

FIELD

The disclosure pertains to systems and methods for transdermal drug delivery, and, in particular, to systems and methods for making and using dissolvable microneedle arrays.

BACKGROUND

The remarkable physical barrier function of the skin poses a significant challenge to transdermal drug delivery. To address this challenge, a variety of microneedle-array based drug delivery devices have been developed. For example, one conventional method employs solid or hollow microneedles arrays with no active component. Such microneedle arrays can pre-condition the skin by piercing the stratum corneum and the upper layer of epidermis to enhance percutaneous drug penetration prior to topical application of a biologic-carrier or a traditional patch. This method has been shown to significantly increase the skin's permeability; however, this method provides only limited ability to control the dosage and quantity of delivered drugs or vaccine.

Another conventional method uses solid microneedles that are surface-coated with a drug. Although this method provides somewhat better dosage control, it greatly limits the quantity of drug delivered. This shortcoming has limited the widespread application of this approach and precludes, for example, the simultaneous delivery of optimal quantities of combinations of antigens and/or adjuvant in vaccine applications.

Another conventional method involves using hollow microneedles attached to a reservoir of biologics. The syringe needle-type characteristics of these arrays can significantly increase the speed and precision of delivery, as well as the quantity of the delivered cargo. However, complex fabrication procedures and specialized application settings limit the applicability of such reservoir-based microneedle arrays.

Yet another conventional method involves using solid microneedle arrays that are biodegradable and dissolvable. This method combines the physical toughness of solid microneedles with relatively high bioactive material capacity, while retaining desired attributes of simple fabrication, storage and application. Current fabrication approaches for dissolvable polymer-based microneedles generally use microcasting processes. For example, a primary mastermold is commonly produced using a combination of complex lithographic and laser etching technologies. However, lithographic and laser-based technologies are limited in the range of geometric features they can create, and the materials to which they can be applied. Also, these highly complex fabrication technologies do not allow rapid or low cost fabrication of mastermolds, which can be particularly useful for systematic testing of the bio-effectiveness of various different microneedle and array geometries.

Accordingly, although transdermal delivery of biologics using microneedle-array based devices offers attractive theoretical advantages over prevailing oral and needle-based drug delivery methods, considerable practical limitations exist in the design, fabrication, and testing associated with microneedle arrays constructed using conventional processes.

SUMMARY

The systems and methods disclosed herein include cutaneous delivery platforms based on dissolvable microneedle arrays that can provide efficient, precise, and reproducible delivery of biologically active molecules to human skin. The microneedle array delivery platforms can be used to deliver a broad range of bioactive components to a patient.

In one embodiment, novel fabrication processes are provided for producing microneedle arrays by micromilling a mastermold, forming a production mold, and spin-casting material (including bioactive components) into the production mold to create a microneedle array. Such processes are flexible and enable simple and rapid low cost production with efficient scale-up potential. Further, because microneedles in these arrays can be configured to not penetrate to the depth of vascular or neural structures, delivery to human skin of bioactive components can be substantially painless and bloodless.

In one embodiment, a method of forming a mastermold for fabricating a microneedle array is provided. The method can include providing a sheet of material; and micromilling the sheet of material to form a mastermold having a base portion, a plurality of projections extending from the base portion, and a fillet portion between each of the projections and the base portion.

In another embodiment, a microneedle array can be formed by directly micromilling a block or sheet of material. The method includes forming a sheet of material having a plurality of layers and micromilling the sheet of material to form a microneedle array. At least one of the plurality of layers has a bioactive component. The microneedle array can have a base portion and plurality of microneedles extending from the base portion.

In specific implementations, the plurality of layers can include a dissoluble biocompatible material. The dissoluble biocompatible material can be carboxymethylcellulose. In other specific implementations, the act of forming a sheet of material can include the acts of providing a layer of a hydrogel of carboxymethylcellulose to create a base layer of a substantially uniform thickness; drying the base layer until the base layer is substantially solid; providing one or more active layers above the base layer with a substantially uniform thickness, a hydrogel of carboxymethylcellulose, and a bioactive component; and drying the one or more active layers until the one or more active layers are substantially solid.

In specific implementations, the act of micromilling includes micromilling the sheet of material to form a plurality of microneedles that are generally pyramidal in shape. In other specific implementations, the act of micromilling includes micromilling the sheet of material to form a plurality of pillar microneedles. Each pillar microneedle can include a generally pyramidal section at a top portion of the microneedle and a generally rectangular section at a bottom portion of the microneedle.

In other specific implementations, the act of micromilling includes micromilling a fillet portion on each microneedle. The fillet portion can be located at the area where the microneedle contacts the base portion of the microneedle array. In other specific implementations, the act of micromilling the sheet comprises forming each microneedle so that it comprises a first cross-sectional dimension at a top portion, a second cross-sectional area at a bottom portion, and a third cross-sectional dimension at an intermediate portion. The intermediate portion is located between the top portion and the bottom portion, and the third cross-sectional dimension is greater than the first and second cross-sectional dimensions.

In other specific implementations, the bioactive component can include at least two different bioactive components. The bioactive component can comprise an antigen and an adjuvant for a vaccine application.

In another embodiment, a dissolvable microneedle array can include a base portion and a plurality of microneedles. Each microneedle can include a first cross-sectional dimension at a top portion, a second cross-sectional dimension at a bottom portion, and a third cross-sectional dimension at an intermediate portion. The intermediate portion is located between the top portion and the bottom portion, and the third cross-sectional dimension is greater than the first and second cross-sectional dimensions.

In specific implementations, the top portion can include a bioactive component. In other specific embodiments, each microneedle can generally taper to a point above the intermediate portion and each microneedle can generally taper to a smaller cross-sectional dimension below the intermediate portion.

In other specific implementations, each microneedle can include a fillet portion located at the area where each microneedle contacts the base portion. In other specific implementations, each microneedle can include a plurality of layers of dissoluble biocompatible material. The dissoluble biocompatible material can be carboxymethylcellulose. In other specific implementations, the bioactive component can include at least two different bioactive components. The bioactive component can include an antigen and an adjuvant for a vaccine application.

In some embodiments, the bioactive components can comprise dissoluble materials or insoluble but dispersible materials. The bioactive components can be natural or formulated macro, micro and nano particulates. The bioactive components can also comprise mixtures of two or more of dissoluble, dispersible insoluble materials and natural and/or formulated macro, micro and nano particulates.

The structural and manufacturing advantages described herein, coupled with a final product that can be stable at room temperature, and inexpensive to transport and store, produce a microneedle array that can be used for broad and rapid clinical deployment. Taken together, these features can provide an affordable and clinically feasible cutaneous delivery technology capable of delivering a range of therapeutic agents, such as vaccines useful in the prevention, treatment, or control of a broad range of human diseases.

In certain embodiments, the microneedle arrays described herein can be used for immunization procedures. In specific implementations, the flexible delivery platforms can be used to efficiently and simultaneously deliver both antigens and adjuvants to skin resident dendritic cells, enabling both targeted antigen delivery and adjuvant engineering of the immune response using the same delivery platform.

The foregoing and other objects, features, and advantages of the disclosed embodiments will become more apparent from the following detailed description, which proceeds with reference to the accompanying figures.

BRIEF DESCRIPTION OF THE DRAWINGS

FIGS. 19A and 19B show induction of apoptosis in epidermal cells that have been delivered CYTOXAN® (cyclophosphamide) through a microneedle array.

FIG. 20 illustrates various microneedle geometries that can be formed using micromilled mastermolds or by direct micromilling of a block of material.

FIG. 21 illustrates a microneedle geometry that can be formed by direct micromilling of a block of material.

FIG. 22 is a stereo microscopic image of a direct-fabricated solid CMC-microneedle array.

FIG. 23 is a stereo microscopic image of a portion of the microneedle array of FIG. 22.

FIG. 26 is a table depicting the transfer of $^3$H-labeled CMC-microneedle material into human skin explants by pyramidal and pillar-type needles.

DETAILED DESCRIPTION

Figure 1:
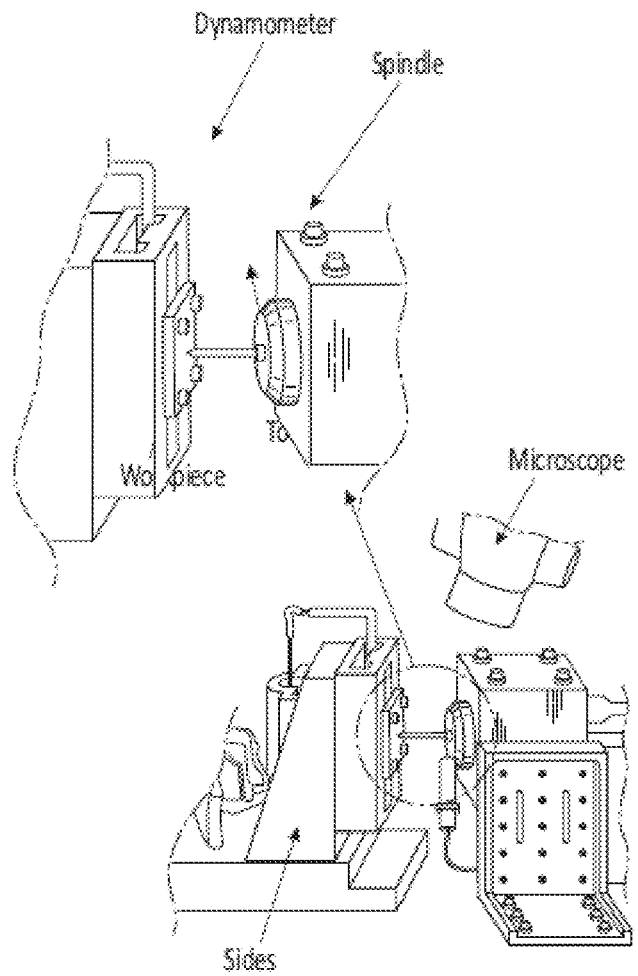
FIG. 1 illustrates a miniature precision-micromilling system used for fabricating microneedle mastermolds.

The following description is exemplary in nature and is not intended to limit the scope, applicability, or configuration of the disclosed embodiments in any way. Various changes to the described embodiment may be made in the function and arrangement of the elements described herein without departing from the scope of the disclosure.

As used in this application and in the claims, the singular forms "a," "an," and "the" include the plural forms unless the context clearly dictates otherwise. Additionally, the term "includes" means "comprises." As used herein, the term "biologic," "active component," or "bioactive material" refers to pharmaceutically active agents, such as analgesic agents, anesthetic agents, anti-asthmatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The bioactive material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates.

As used herein, the term "pre-formed" means that a structure or element is made, constructed, and/or formed into a particular shape or configuration prior to use. Accordingly, the shape or configuration of a pre-formed microneedle array is the shape or configuration of that microneedle array prior to insertion of one or more of the microneedles of the microneedle array into the patient.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Micromilled Master Molds and Spin-Molded Microneedle Arrays

In a first embodiment, apparatuses and methods are described for fabricating dissolvable microneedle arrays using master molds formed by micromilling techniques. For example, microneedle arrays can be fabricated based on a mastermold (positive) to production mold (negative) to array (positive) methodology. In contrast to the formation of conventional mastermolds used to create microneedle arrays, micromilling technology can be used to generate various micro-scale geometries on virtually any type of material, including metal, polymer, and ceramic parts. Micromilled mastermolds of various shapes and configurations can be effectively used to generate multiple identical female production molds. The female production molds can then be used to microcast various microneedle arrays.

Direct micromilling of mastermolds can replace expensive, complex and equipment-sensitive SU-8 based lithography or laser etching techniques, which are conventionally used to create mastermolds for dissolvable needle arrays. In addition, as discussed below, micromilling can provide for the construction of more complex mastermold features than can conventional lithography and laser etching processes.

FIG. 1 illustrates an example of a precision-micromilling system that can be used for fabricating a microneedle mastermold. Mechanical micromilling uses micro-scale (for example, as small as 10 μm) milling tools within precision computer controlled miniature machine-tool platforms. The system can include a microscope to view the surface of the workpiece that is being cut by the micro-tool. The micro-tool can be rotated at ultra-high speeds (200,000 rpm) to cut the workpiece to create the desired shapes.

As noted above, the micromilling process can be used to create complex geometric features with many kinds of material, which are not possible using conventional lithographic or laser etching processes. Various types of tooling can be used in the micromilling process, including, for example, carbide micro-tools. In a preferred embodiment, however, diamond tools can be used to fabricate the microneedle arrays on the master mold. Diamond tooling can be preferable over other types of tooling because it is harder than conventional materials, such as carbide, and can provide cleaner cuts on the surface of the workpiece.

Figures 2A, 2B:
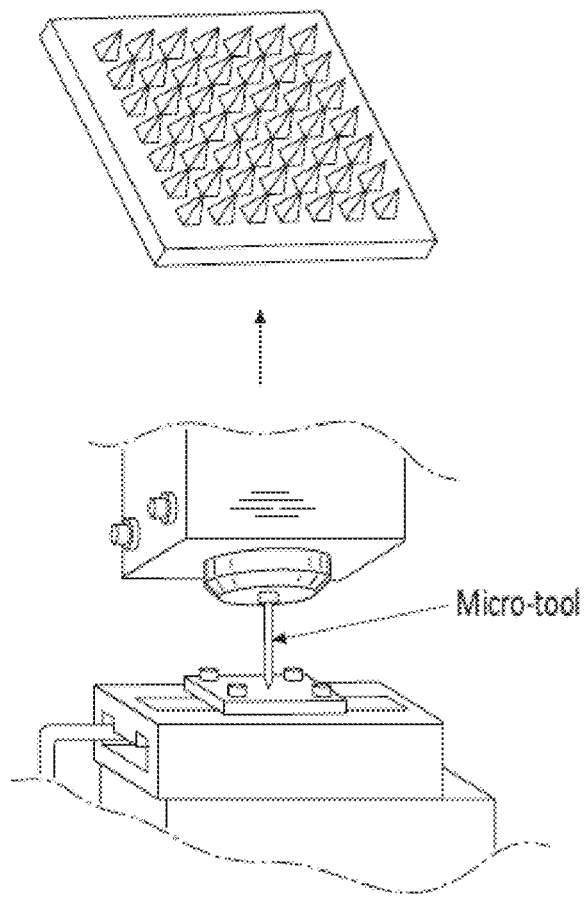
FIG. 2A is an enlarged view of a work-surface area of the micro-milling system.
FIG. 2B is a schematic representation of the milled mastermold.

FIG. 2A illustrates a portion of the precision-micromilling system shown in FIG. 1. In particular, FIG. 2A shows a workpiece that is being micromilled by a micro-tool. FIG. 2B shows a schematic enlarged view of a completed micromilled workpiece (i.e., a directly micromilled mastermold). As discussed in more detail below, the completed micromilled workpiece can be a mastermold that has a plurality of pyramidal projections extending from a base surface of the workpiece.

Mastermolds can be micromilled from various materials, including, for example, CIRLEX® (DuPont, KAPTON® polyimide), which is the mastermold material described in the exemplary embodiment. Mastermolds can be used to fabricate flexible production molds from a suitable material, such as SYLGARD® 184 (Dow Corning, silicone elastomer), which is the production material described in the exemplary embodiment below. The mastermold is desirably formed of a material that is capable of being reused so that a single mastermold can be repeatedly used to fabricate a large number of production molds. Similarly each production mold is desirably able to fabricate multiple microneedle arrays.

Mastermolds can be created relatively quickly using micromilling technology. For example, a mastermold that comprises a 10 mm×10 mm array with 100 microneedles can take less than a couple of hours and, in some embodiments, less than about 30 minutes to micromill. Thus, a short ramp-up time enables rapid fabrication of different geometries, which permits the rapid development of microneedle arrays and also facilitates the experimentation and study of various microneedle parameters.

The mastermold material preferably is able to be cleanly separated from the production mold material and preferably is able to withstand any heighted curing temperatures that may be necessary to cure the production mold material. For example, in an illustrated embodiment, the silicone-based compound SYLGARD® 184 (Dow Corning) is the production mold material and that material generally requires a curing temperature of about 80-90 degrees Celsius.

Mastermolds can be created in various sizes. For example, in an exemplary embodiment, a mastermold was created on 1.8 mm thick CIRLEX® (DuPont, KAPTON® polyimide) and 5.0 mm thick acrylic sheets. Each sheet can be flattened first by micromilling tools, and the location where the microneedles are to be created can be raised from the rest of the surface. Micro-tools can be used in conjunction with a numerically controlled micromilling machine (FIG. 1) to create the microneedle features (e.g., as defined by the mastermold). In that manner, the micromilling process can provide full control of the dimensions, sharpness, and spatial distribution of the microneedles.

Figure 3:
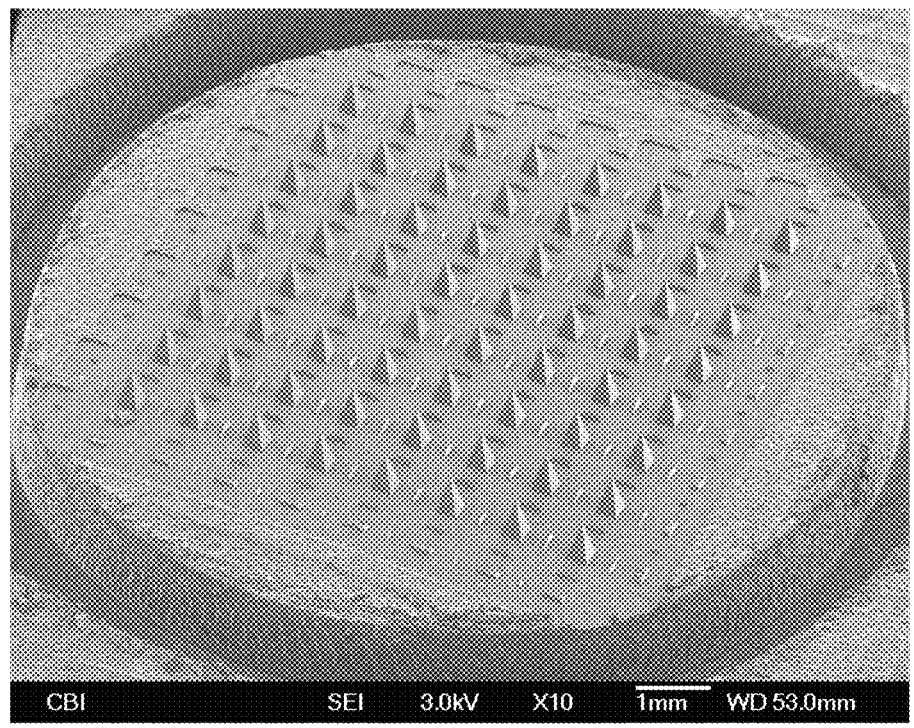
FIG. 3 is an SEM image of a micromilled mastermold with pyramidal needles.

As shown in FIG. 3, a circular groove can be formed around the microneedle array of the mastermold to produce an annular (for example, circular) wall section in the production mold. The circular wall section (FIG. 5) of the production mold can facilitate the spincasting processes discussed below.

Figure 4:
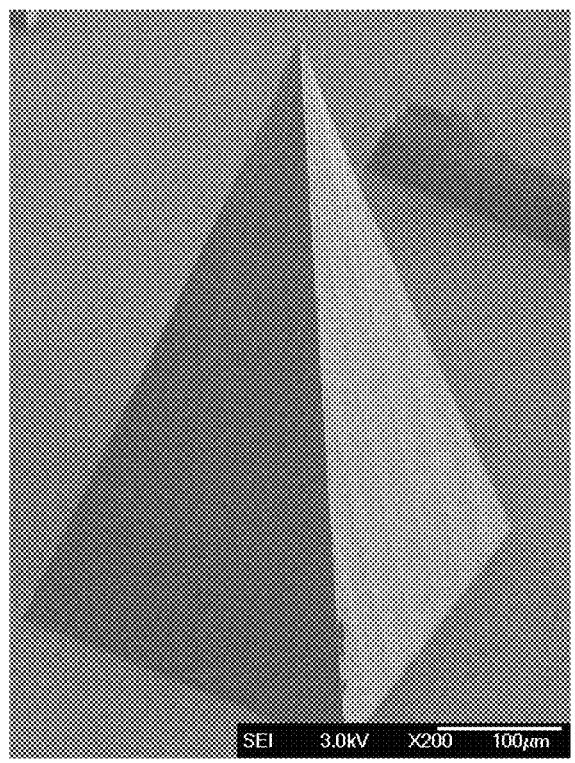
FIG. 4 is an SEM image of a pyramidal needle shown in FIG. 3.

FIG. 3 is an image from a scanning electron microscope (SEM) showing the structure of a micromilled mastermold with a plurality of pyramidal needles. FIG. 4 illustrates an enlarged view of a pyramidal needle of FIG. 3.

Figure 5:
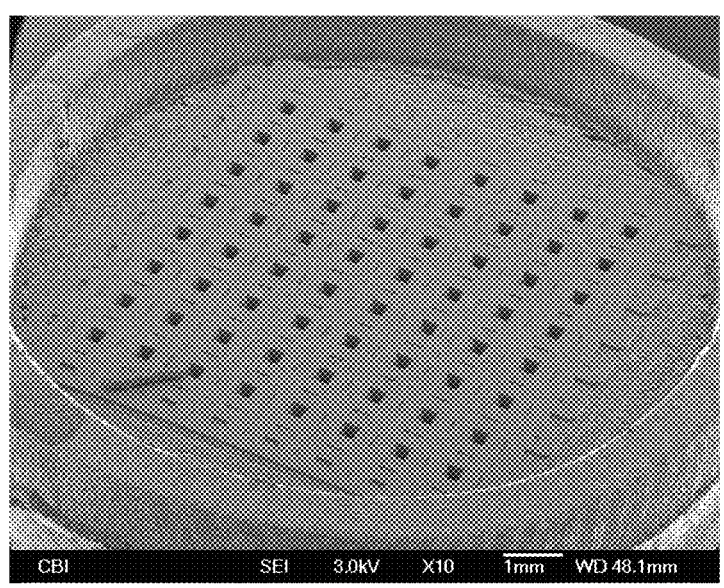
FIG. 5 is an SEM image of a pyramidal production mold.

As discussed above, the production molds can be made from SYLGARD® 184 (Dow Corning, silicone elastomer), which is a two component clear curable silicone elastomer that can be mixed at a 10:1 SYLGARD® (Dow Corning, silicone elastomer) to curing agent ratio. The mixture can be degassed for about 10 minutes and poured over the mastermold to form an approximately 8 mm layer, subsequently degassed again for about 30 minutes and cured at 85° C. for 45 minutes. After cooling down to room temperature, the mastermold can be separated from the cured silicone, and the silicone production mold trimmed to the edge of the circular wall section that surrounds the array (FIG. 5.). From a single mastermold, a large number of production molds (e.g., 100 or more) can be produced with very little, if any, apparent deterioration of the CIRLEX® (DuPont, KAPTON®) polyimide) or acrylic mastermolds.

Figure 6:
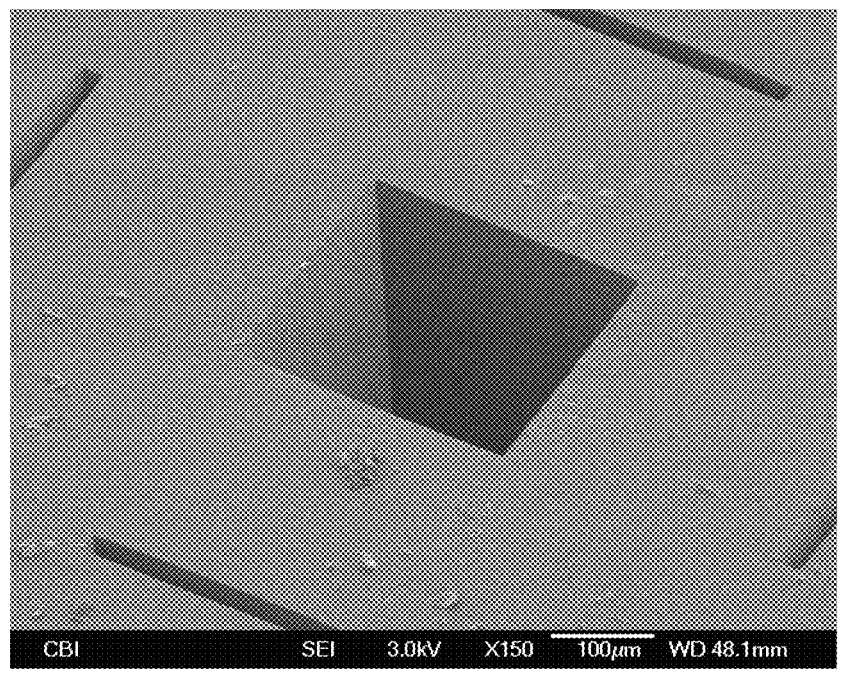
FIG. 6 is an SEM image of an enlarged segment of the production mold, illustrating a pyramidal needle molding well in the center of the image.

FIG. 5 is an SEM image of a pyramidal production mold created as described above. FIG. 6 illustrates an enlarged segment of the production mold with a pyramidal needle molding well in the center of the image. The molding well is configured to receive a base material (and any components added to the base material) to form microneedles with an external shape defined by the molding well.

To construct the microneedle arrays, a base material can be used to form portions of each microneedle that have bioactive components and portions that do not. Of course, if desired, each microneedle can comprise only portions that contain bioactive components; however, to control the delivery of the bioactive component(s) and to control the cost of the microneedle arrays, each microneedle preferably has a portion with a bioactive component and a portion without a bioactive component.

Various materials can be used as the base material for the microneedle arrays. The structural substrates of biodegradable solid microneedles most commonly include poly(lactic-co-glycolic acid) (PLGA) or carboxymethylcellulose (CMC) based formulations; however, other bases can be used.

CMC is generally preferable to PLGA as the base material of the microneedle arrays described herein. The PLGA based devices can limit drug delivery and vaccine applications due to the relatively high temperature (e.g., 135 degrees Celsius or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components.

CMC-hydrogel can be prepared from low viscosity sodium salt of CMC with or without active components (as described below) in sterile $dH_2O$. In the exemplary embodiment, CMC can be mixed with sterile distilled water ($dH_2O$) and with the active components to achieve about 25 wt % CMC concentration. The resulting mixture can be stirred to homogeneity and equilibrated at about 4 degrees Celsius for 24 hours. During this period, the CMC and any other components can be hydrated and a hydrogel can be formed. The hydrogel can be degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85 degrees Celsius for about 72 hours. The ready-to-use CMC-hydrogel is desirably stored at about 4 degrees Celsius until use.

Active components can be incorporated in a hydrogel of CMC at a relatively high (20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4 degrees Celsius), and preserve the activity of the incorporated biologics, facilitating easy, low cost storage and distribution.

In an exemplary embodiment, the surface of the production molds can be covered with about 50 μl (for molds with 11 mm diameter) of CMC-hydrogel and spin-casted by centrifugation at 2,500 g for about 5 minutes. After the initial CMC-hydrogel layer, another 50 CMC-hydrogel can be layered over the mold and centrifuged for about 4 hours at 2,500 g. At the end of a drying process, the CMC-microneedle arrays can be separated from the molds, trimmed off from excess material at the edges, collected and stored at about 4 degrees Celsuis. The production molds can be cleaned and reused for further casting of microneedle arrays.

Figures 7A, 7B:
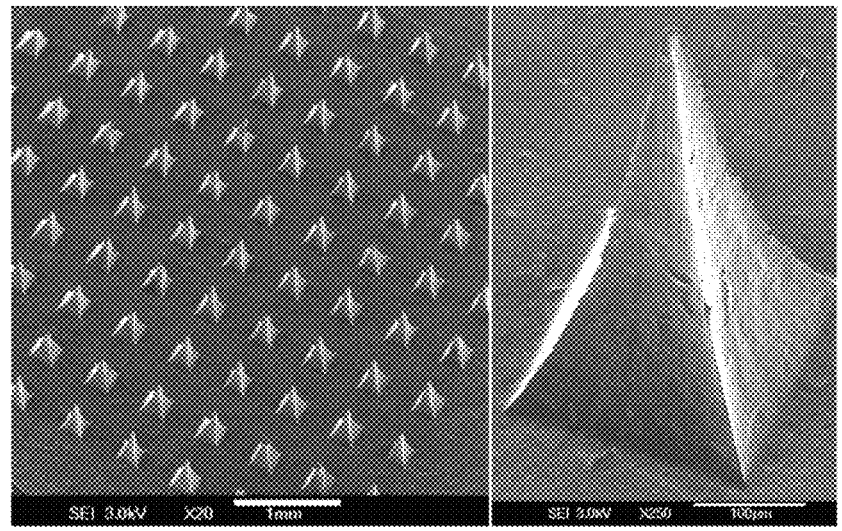
FIG. 7A is an SEM image of a plurality of pyramidal-type molded microneedles.
FIG. 7B is an SEM image of a single pyramidal-type molded microneedle.

FIGS. 7A and 7B are SEM images of a CMC-microneedle array formed with a plurality of pyramidal projections (i.e., microneedles). The average tip diameter of the pyramidal needles shown in FIG. 7A is about 5-10 µm. As shown in FIG. 7B, the sides of the pyramidal needles can be formed with curved and/or arcuate faces that can facilitate insertion in skin.

Figure 8:
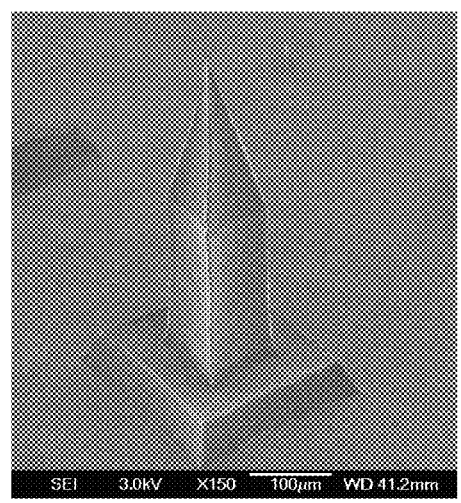
FIG. 8 is an SEM image of a pillar type molded microneedle.

FIG. 8 is another SEM image of a single needle of a microneedle array. The microneedle shown in FIG. 8 is a base-extended pillar type molded CMC-microneedle. The base-extended pillar type microneedle comprises a base portion, which is generally polyagonal (for example, rectangular) in cross section, and a projecting portion that extends from the base portion. The projecting portion has a lower portion that is substantially rectangular and tip portion that generally tapers to a point. The tip portion is generally pyramidal in shape, and the exposed faces of the pyramid can be either flat or arcuate. The projecting portion can be half or more the entire length of the needle.

Figure 9:
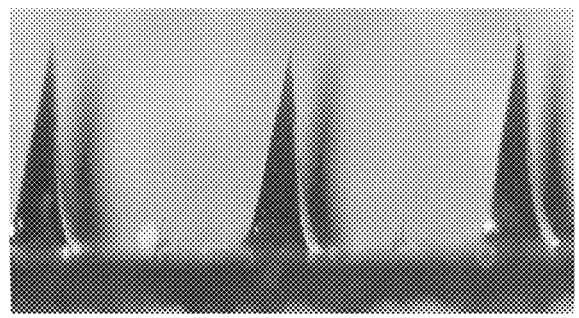
FIG. 9 is a micrograph of pyramidal type molded microneedles.
Figure 10:
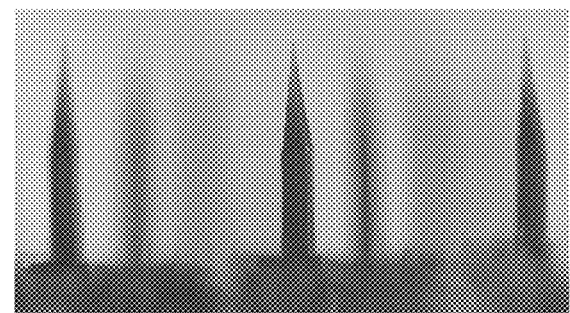
FIG. 10 is a micrograph of pillar type molded microneedles.

FIGS. 9 and 10 illustrate micrographs of pyramidal (FIG. 9) and pillar type (FIG. 10) molded CMC-microneedles. Because the pyramidal needles have a continually increasing cross-sectional profile (dimension) from the needle point to the needle base, as the needle enters the skin, the force required to continue pushing the pyramidal needle into the skin increases. In contrast, pillar type needles have a generally continuous cross-sectional profile (dimension) once the generally rectangular portion of the projection portion is reached. Thus, pillar type needles can be preferable over pyramidal type needles because they can allow for the introduction of the needle into the skin with less force.

FIG. 20 illustrates schematic representation of microneedle shapes and structures that are generally suitable for fabrication by spin-casting material into a mastermold formed by micromilling. Since the shapes and structures shown in FIG. 20 do not contain any undercuts, they generally will not interfere with the molding/de-molding process. The structures in FIG. 20 include (a) a generally pyramidal microneedle, (b) a "sharp" pillar type microneedle (without the base member of FIG. 8), (c) a "wide" pillar type microneedle, (d) a "short" pillar type microneedle (having a short pillar section and a longer pointed section), and (e) a "filleted" pillar type microneedle.

While the volume of the pyramidal microneedles can be greater than that of the pillar type microneedles, their increasing cross-sectional profile (dimension) requires an increasing insertion force. Accordingly, the geometry of the pyramidal microneedles can result in reduced insertion depths and a reduced effective delivery volume. On the other hand, the smaller cross-sectional area and larger aspect ratio of the pillar microneedles may cause the failure force limit to be lower. The smaller the apex angle α, the "sharper" the tip of the microneedle. However, by making the apex angle too small (e.g., below about 30 degrees), the resulting microneedle volume and mechanical strength may be reduced to an undesirable level.

The penetration force of a microneedle is inversely proportional to the microneedle sharpness, which is characterized not only by the included (apex) angle of the microneedles, but also by the radius of the microneedle tip. While the apex angle is prescribed by the mastermold geometry, the tip sharpness also depends on the reliability of the mold. Micromilling of mastermolds as described herein allows for increased accuracy in mold geometry which, in turn, results in an increased accuracy and reliability in the resulting production mold and the microneedle array formed by the production mold.

The increased accuracy of micromilling permits more accurate and detailed elements to be included in the mold design. For example, as discussed in the next section below, the formation of a fillet at the base of a pillar type microneedle can significantly increase the structural integrity of the microneedle, which reduces the likelihood that the microneedle will fail or break when it impacts the skin. While these fillets can significantly increase the strength of the microneedles, they do not interfere with the functional requirements of the microneedles (e.g., penetration depth and biologics volume). Such fillets are very small features that can be difficult to create in a master mold formed by conventional techniques. However, the micromilling techniques described above permit the inclusion of such small features with little or no difficulty.

Mechanical Integrity and Penetration Capabilities

Microneedle arrays are preferably configured to penetrate the stratum corneum to deliver their cargo (e.g., biologics or bioactive components) to the epidermis and/or dermis, while minimizing pain and bleeding by preventing penetration to deeper layers that may contain nerve endings and vessels. To assess the mechanical viability of the fabricated microneedle arrays, tests were performed on the pyramidal and pillar type microneedle arrays as representative variants of array geometry (shown, e.g., in FIGS. 7B and 8). The first set of tests illustrate the failure limit of microneedles, and include pressing the microneedle array against a solid acrylic surface with a constant approach speed, while simultaneously measuring the force and the displacement until failure occurs. The second set of tests illustrate the piercing capability of the microneedles on human skin explants.

Figure 11:
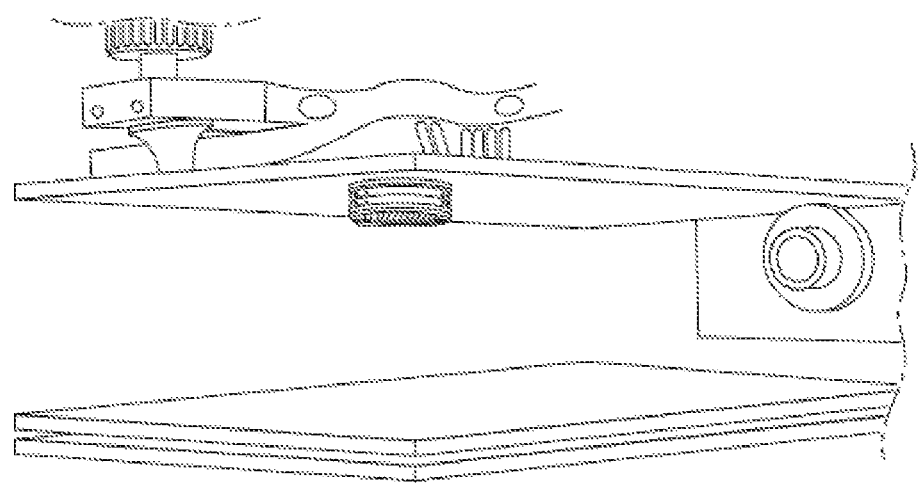
FIG. 11 illustrates a test apparatus for performing failure and piercing tests.

FIG. 11 illustrates a test apparatus designed for functional testing. The sample (i.e., microneedle array) was attached to a fixture, which was advanced toward a stationary acrylic artifact (PMMA surface) at a constant speed of about 10 mm/s speed using a computer-controlled motion stage (ES14283-52 Aerotech, Inc.). A tri-axial dynamometer (9256C1, Kistler, Inc.) that hosted the acrylic artifact enabled high-sensitivity measurement of the forces.

Figure 12:
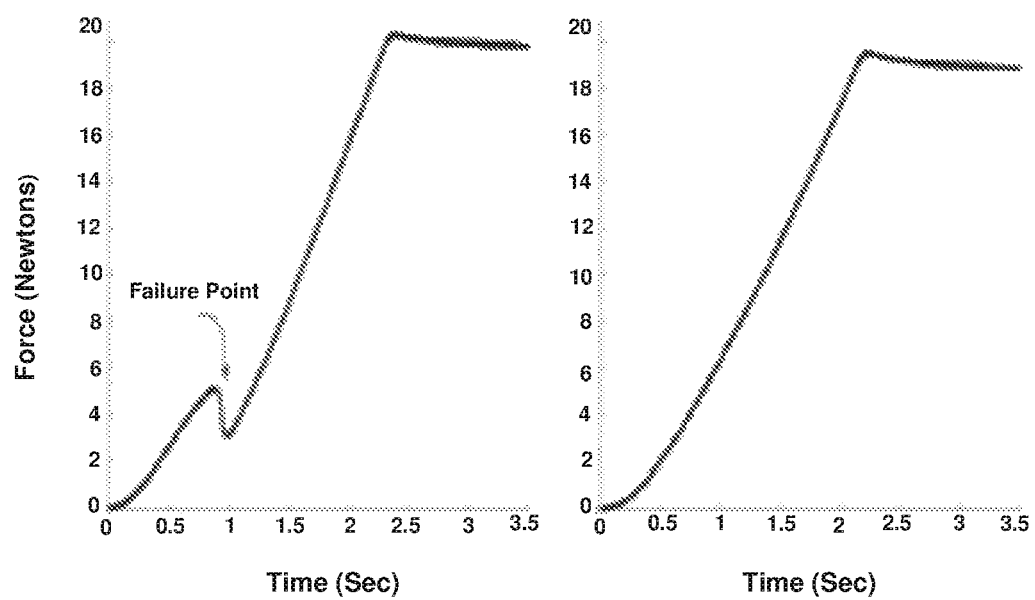
FIG. 12 illustrates force-displacement curves for pillar type microneedles (left) and pyramidal type microneedles (right).

FIG. 12 illustrates force-displacement curves of data measured during failure tests. The curve on the left is representative of data obtained from testing a pillar microneedle sample and the curve on the right is representative of data obtained from testing a pyramid microneedle. As seen in FIG. 12, the failure of these two kinds of microneedles are significantly different; while the pyramidal arrays plastically deform (bend), the pillar type arrays exhibit breakage of the pillars at their base. This different failure behavior lends itself to considerably different displacement-force data. The failure (breakage) event can be easily identified from the displacement-force data as indicated in the figure. Based on the obtained data, the failure point of pillar type microneedles was seen to be 100 mN in average. As only about 40 mN of force is required for penetration through the stratum corneum, the microneedles are strong enough to penetrate human skin without failure. Furthermore, since parallelism between microneedle tips and the acrylic artifact cannot be established perfectly, the actual failure limit will likely be significantly higher than 100 mN (i.e., microneedles broke in a successive manner, rather than simultaneous breakage of most/all microneedles).

The pyramidal microneedles presented a continuously increasing force signature with no clear indication of point of failure. To identify the failure limit for the pyramidal microneedles, interrupted tests were conducted in which the microneedles were advanced into the artifact by a certain amount, and retreated and examined through optical microscope images. This process was continued until failure was observed. For this purpose, the failure was defined as the bending of the pyramidal microneedles beyond 15 degrees.

Figure 13:
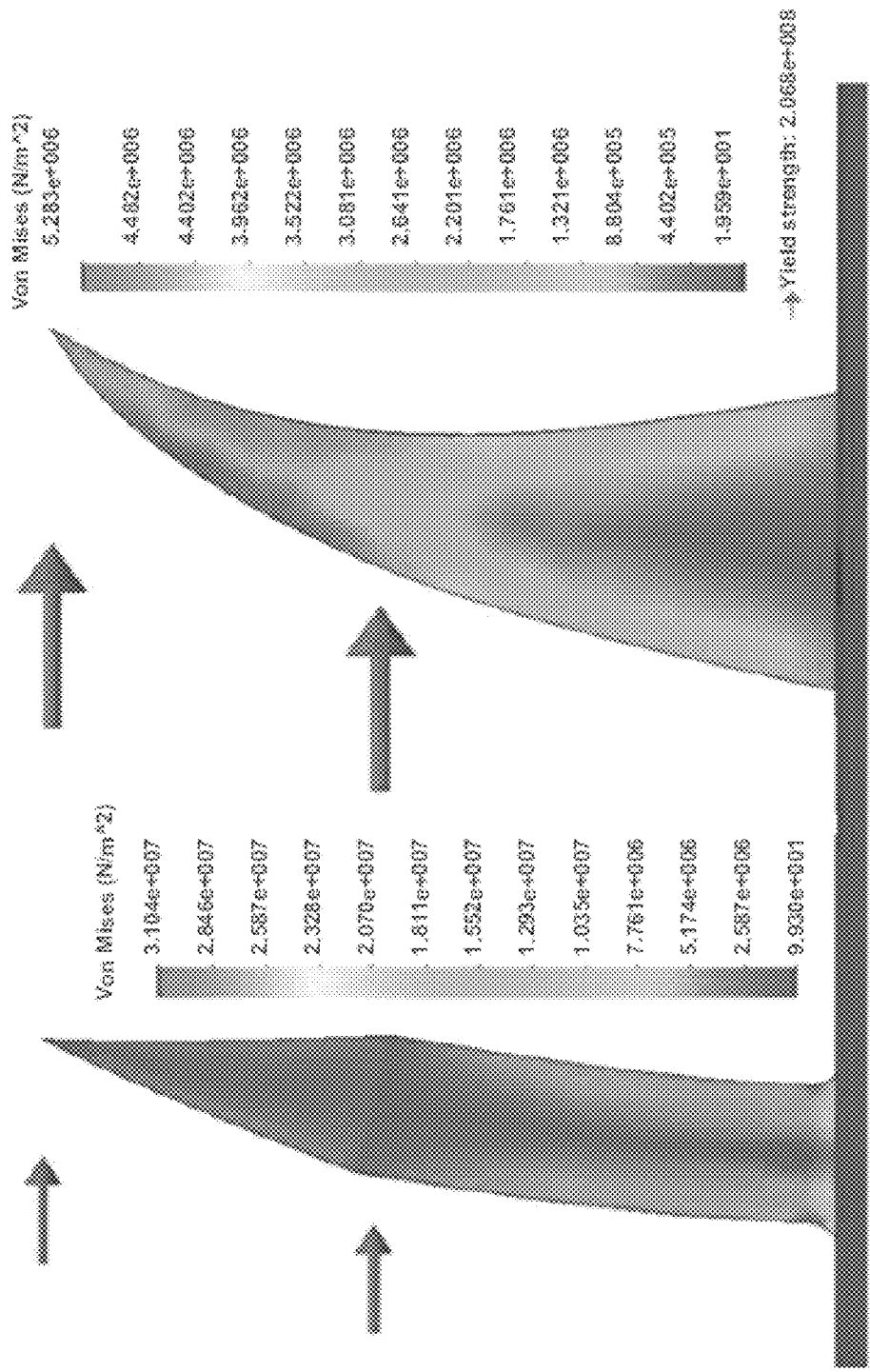
FIG. 13 illustrates a finite elements model of microneedle deflections for pillar type microneedles (left) and pyramidal type microneedles (right).

To further analyze the failure of the microneedles, the finite-elements model (FEM) of the microneedle arrays shown in FIG. 13 was developed. To obtain the mechanical properties (elastic modulus and strength limit) of the CMC material, a series of nanoindentation tests (using a Hysitron nanoindentor). The average elastic modulus and yield strength of the CMC material (as prepared) were 10.8 GPa and 173 MPa, respectively. This indicates that the prepared CMC material has a higher elastic modulus and yield strength than both PMMA (elastic modulus: 3.1 GPa, yield strength: 103 MPa) and polycarbonate (elastic modulus: 2.2 GPa, yield strength: 75 MPa), indicating the superior strength and stiffness of CMC material with respect to other polymers.

Using this data, a series of FEM simulations were conducted. It was predicted from the FEM models that failure limit of pyramidal and sharp-pillar (width=134 µm) microneedles with 600 µm height, 30 degree apex angle, and 20 µm fillet radius were 400 mN (pyramid) and 290 mN (sharp-pillar) for asymmetric loading (5 degrees loading misorientation). Considering that the minimum piercing force requirement is about 40 mN, pyramid and sharp-pillar microneedles would have factors of safety of about 10 and 7.25, respectively.

When the fillet radius is doubled to 40 µm, the failure load for the pillar was increased to 350 mN, and when the fillet radius is reduced to 5 µm, the failure load was reduced to 160 mN, which is close to the experimentally determined failure load. The height and width of the pillars had a significant effect on failure load. For instance, for 100 µm width pillars, increasing the height from 500 µm to 1000 µm reduced the failure load from 230 mN to 150 mN. When the width is reduced to 75 µm, for a 750 µm high pillar, the failure load was seen to be 87 mN.

Figure 14:
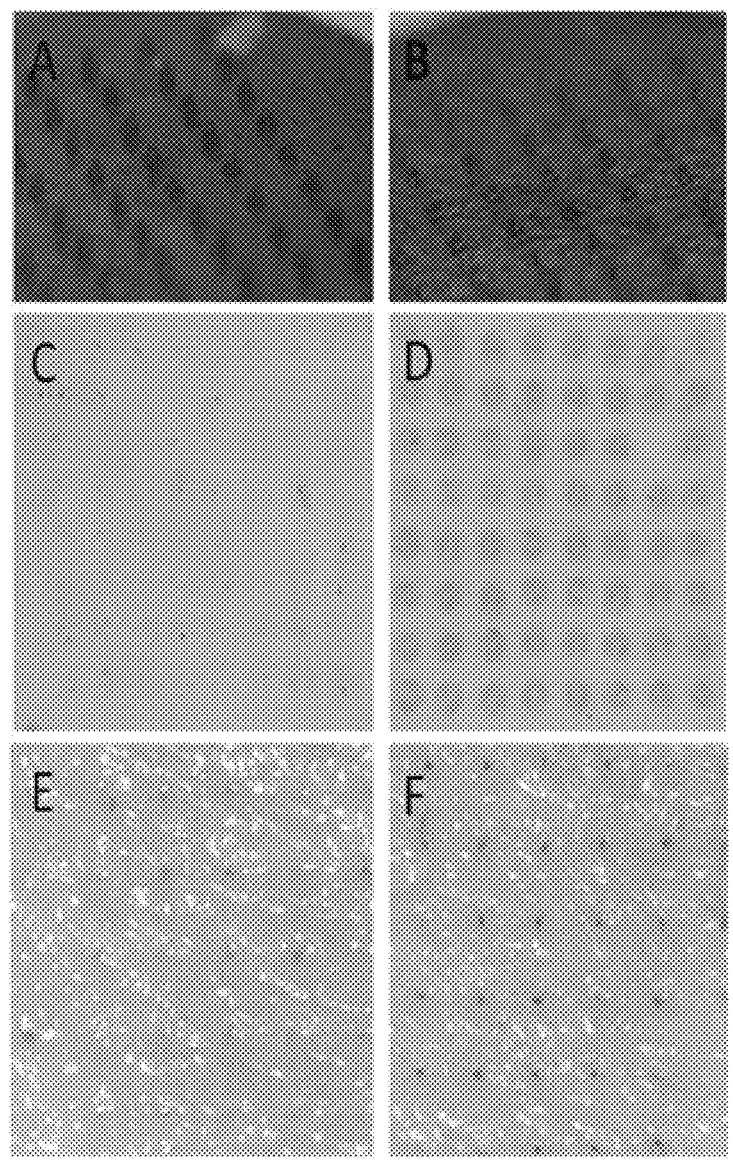
FIG. 14 show various stereo micrographs of the penetration of pyramidal (A, C, E) and pillar (B, D, F) type microneedles in skin explants.

To evaluate penetration capability, pyramidal and sharp-pillar microneedle arrays were tested for piercing on water-based model elastic substrates and on full thickness human skin. FIG. 14 illustrates stereo micrographs of pyramidal (Panels A, C, and E) and pillar type microneedle arrays (B, D, and F) after 4 minutes of exposure to model elastics. In particular, toluene blue tracer dye was deposited in model elastic substrates (Panels C and D) or freshly excised full thickness human skin explants (Panels E and F) after application of pyramidal or pillar type microneedle arrays.

The model elastic substrate comprised about 10% CMC and about 10% porcine gelatin in PBS gelled at about 4 degrees Celsius for about 24 hours or longer. The surface of the elastics was covered with about 100 µm thick parafilm to prevent the immediate contact of the needle-tips and the patch materials with the water based model elastics. To enable stereo microscopic-imaging, trypan blue tracer dye (Sigma Chem., cat #T6146) was incorporated into the CMC-hydrogel at 0.1% concentration. The patches were applied using a spring-loaded applicator and analyzed after about a 4 minute exposure. Based on physical observation of the dye in the target substrates, the dissolution of the microneedles of the two different geometries was markedly different.

The sharp-pillar needles applied to the model elastic substrate released substantially more tracer dye to the gel matrix than that observed for the pyramidal design (FIG. 14, C vs. D). Images of the recovered patches (FIG. 14, A vs. B) were consistent with this observation, as the degradation of the sharp-pillar needles was more advanced than that of the pyramidal needles. To extrapolate this analysis to a more clinically relevant model, pyramidal and pillar type microneedle arrays were applied to freshly excised full thickness human skin explants using the same force from the spring loaded applicator. Consistent with results from the elastic model, the pyramidal microneedle arrays deposited visibly less tracer dye than the sharp-pillar microneedle arrays (FIG. 14, E vs. F).

To further evaluate penetration and to assess delivery effectiveness to human skin, CMC-microneedle arrays were fabricated with BIOMAG® (Polysciences, Inc., cat #. 84100) beads or fluorescent particulate tracers (FLURESBRITE®, YG 1 µm, Polysciences Inc., cat #. 15702). The pyramidal CMC-microneedle arrays containing fluorescent or solid particulates were applied to living human skin explants as described previously. Five minutes after the application, surface residues were removed and skin samples were cryo-sectioned and then counterstained with toluene blue for imaging by light microscopy (FIGS. 15A and 15B) or by fluorescent microscopy (FIG. 15C).

Figures 15A, 15B, 15C:
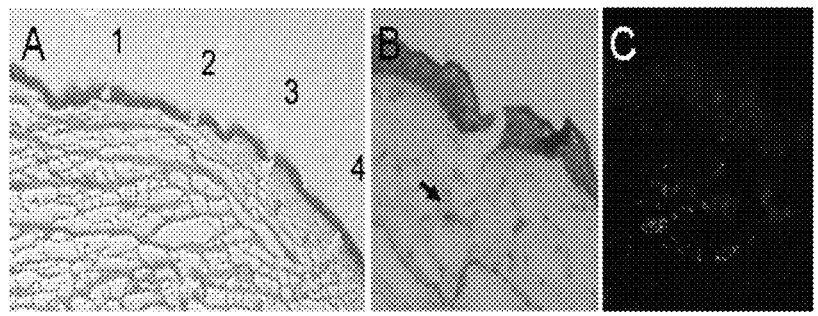
FIGS. 15A, 15B, and 15C illustrate the effectiveness of microneedle arrays in penetrating skin explants.

Pyramidal CMC-microneedles effectively penetrated the stratum corneum, epidermis, and dermis of living human skin explants, as evidenced by the deposition of Biomag beads lining penetration cavities corresponding to individual needle insertion points (representative sections shown in FIGS. 15A and 15B). In particular, ordered cavities (FIG. 15A, cavities numbered 1-4, toluene blue counterstain, 10×) and deposits of BioMag particles (brown) lining penetration cavities were evident (FIG. 15B, 40×), indicating microneedle penetrated of human skin. Further, analysis of sections from living human explants stained with DAPI to identify cell nuclei and anti-HLA-DR to identify MHC class II+ antigen presenting cells revealed high density fluorescent particulates deposited in the superficial epidermis and dermis, including several particles co-localized with class II+ antigen presenting cells (FIG. 15C, DAPI (blue), HLA-DR+ (red) and fluorescent particles (green), 40×).

These results further demonstrate that the CMC microneedle arrays described herein can effectively penetrate human skin and deliver integral cargo (bioactive components), including insoluble particulates. They are consistent with effective delivery of particulate antigens to antigen presenting cells in human skin, currently a major goal of rational vaccine design.

Figures 16A, 16B:
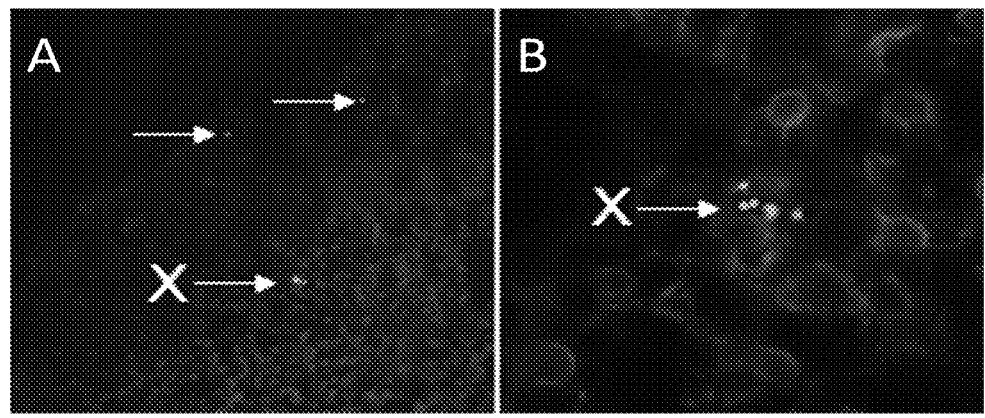
FIGS. 16A and 16B illustrate in vivo delivery of particulates to the skin draining lymph nodes of microneedle array immunized mice.

To further address microneedle array delivery in vivo, the cutaneous delivery of particulate antigen in vivo was modeled by similarly applying fluorescent particle containing arrays to the dorsal aspect of the ears of anesthetized mice. After 5 minutes, patches were removed and mice resumed their normal activity. Three hours or 3 days, ear skin and draining lymph nodes were analyzed for the presence of fluorescent particles. Consistent with observations of human skin, particulates were evident in the skin excised from the array application site (data not shown). Further, at the 3 day time point, substantial numbers of particles were evident in the draining lymph nodes. FIGS. 16A and 16B illustrates substantial numbers of particles that were evident in the draining lymph Nodes (FIG. 16A, 10×), including clusters of particulates closely associated with Class II+ cells (FIG. 16B, 60×) suggesting the presence of lymph node resident antigen presenting cells with internalized particulates.

To quantitatively evaluate the effects of needle geometry on cargo delivery using microneedle arrays, 3H-tracer labeled CMC-microneedle arrays were constructed. The CMC-hydrogel was prepared with 5% wt ovalbumin as a model active component at 25 wt % final dry weight content (5 g/95 g OVA/CMC) and trace labeled with 0.1 wt % trypan blue and 0.5×106 dpm/mg dry weight 3H-tracer in the form of 3H-thymidine (ICN Inc., cat #2406005). From a single batch of labeled CMC-hydrogel-preparation four batches of 3H-CMC-microneedle arrays were fabricated, containing several individual patches of pyramidal and sharp-pillar needle geometry. The patches were applied to human skin explants as described above and removed after 30 min exposure. The patch-treated area was tape-striped to remove surface debris and cut using a 10 mm biopsy punch. The 3H content of the excised human skin explants-discs was determined by scintillation counting. The specific activity of the 3H-CMC-microneedle patch-material was determined and calculated to be 72,372 cpm/mg dry weight. This specific activity was used to indirectly determine the amount of ovalbumin delivered to and retained in the skin. The resulting data is summarized in FIG. 26.

The tested types of patches were consistent from microneedle array to microneedle array (average standard deviation 24-35%) and batch to batch (average standard deviation 7-19%). The intra-batch variability for both needle geometry was lower than the in-batch value indicating that the insertion process and the characteristics of the target likely plays a primary role in the successful transdermal material delivery and retention. The patch-material retention data clearly demonstrate the foremost importance of the microneedle geometry in transdermal cargo delivery. Pillar-type needle geometry afforded an overall 3.89 fold greater deposition of the 3H labeled needle material than that of the pyramidal needles. On the basis of the deposited radioactive material, it is estimated that the pyramidal needles were inserted about 200 µm deep while the pillar-type were inserted about 400 µm or more.

Desirably, the microneedle arrays described herein can be used for cutaneous immunization. The development of strategies for effective delivery of antigens and adjuvants is a major goal of vaccine design, and immunization strategies targeting cutaneous dendritic cells have various advantages over traditional vaccines.

The microneedle arrays described herein can also be effective in chemotherapy and immunochemotherapy applications. Effective and specific delivery of chemotherapeutic agents to tumors, including skin tumors is a major goal of modern tumor therapy. However, systemic delivery of chemotherapeutic agents is limited by multiple well-established toxicities. In the case of cutaneous tumors, including skin derived tumors (such as basal cell, squamous cell, Merkel cell, and melanomas) and tumors metastatic to skin (such as breast cancer, melanoma), topical delivery can be effective. Current methods of topical delivery generally require the application of creams or repeated local injections. The effectiveness of these approaches is currently limited by limited penetration of active agents into the skin, non-specificity, and unwanted side effects.

The microneedle arrays of the present disclosure can be used as an alternative to or in addition to traditional topical chemotherapy approaches. The microneedle arrays of the present disclosure can penetrate the outer layers of the skin and effectively deliver the active biologic to living cells in the dermis and epidermis. Delivery of a chemotherapeutic agents results in the apoptosis and death of skin cells.

Further, multiple bioactive agents can be delivered in a single microneedle array (patch). This enables an immunochemotherapeutic approach based on the co-delivery of a cytotoxic agent with and immune stimulant (adjuvants). In an immunogenic environment created by the adjuvant, tumor antigens releases from dying tumor cells will be presented to the immune system, inducing a local and systemic anti-tumor immune response capable of rejecting tumor cells at the site of the treatment and throughout the body.

In an exemplary embodiment, the delivery of a biologically active small molecule was studied. In particular, the activity of the chemotherapeutic agent CYTOXAN® (cyclophosphamide) delivered to the skin with CMC microneedle arrays was studied. The use of CYTOXAN® (cyclophosphamide) enables direct measurement of biologic activity (CYTOXAN® (cyclophosphamide) induced apoptosis in the skin) with a representative of a class of agents with potential clinical utility for the localized treatment of a range of cutaneous malignancies.

To directly evaluate the immunogenicity of CMC microneedle array incorporated antigens, the well characterized model antigen ovalbumin was used. Pyramidal arrays were fabricated incorporating either soluble ovalbumin (sOVA), particulate ovalbumin (pOVA), or arrays containing both pOVA along with CpGs. The adjuvant effects of CpGs are well characterized in animal models, and their adjuvanticity in humans is currently being evaluated in clinical trials.

Immunization was achieved by applying antigen containing CMC-microneedle arrays to the ears of anesthetized mice using a spring-loaded applicator as described above, followed by removal of the arrays 5 minutes after application. These pyramidal microneedle arrays contained about 5 wt % OVA in CMC and about 0.075 wt % (20 µM) CpG. As a positive control, gene gun based genetic immunization strategy using plasmid DNA encoding OVA was used. Gene gun immunization is among the most potent and reproducible methods for the induction of CTL mediated immune responses in murine models, suggesting its use as a "gold standard" for comparison in these assays.

Figure 17:
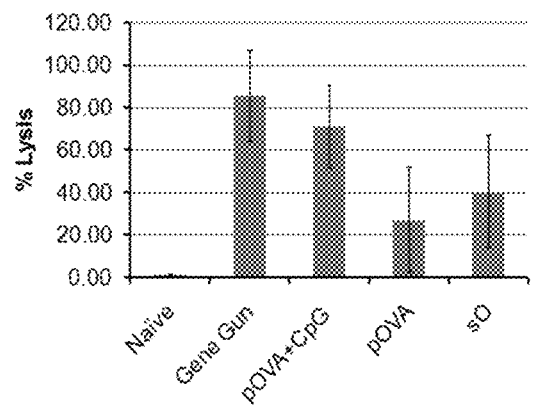
FIG. 17 is a bar graph showing immunogenicity of microneedle delivered model antigens.

Mice were immunized, boosted one week later, and then assayed for OVA-specific CTL activity in vivo. Notably, immunization with arrays containing small quantities of OVA and CpG induced high levels of CTL activity, similar to those observed by gene gun immunization (FIG. 17). Significant OVA-specific CTL activity was elicited even in the absence of adjuvant, both with particulate and soluble array delivered OVA antigen. It is well established that similar responses require substantially higher doses of antigen when delivered by traditional needle injection.

Figure 18:
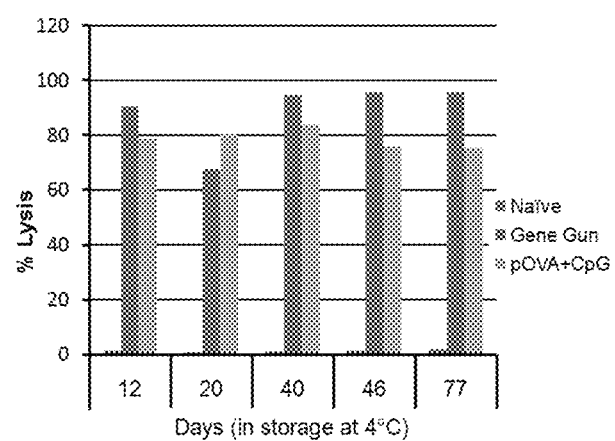
FIG. 18 is a bar graph showing the stability of the active cargo of CMC-microneedle arrays in storage.

To evaluate the stability of fabricated arrays, batches of arrays were fabricated, stored, and then used over an extended period of time. As shown in FIG. 18, no significant deterioration of immunogenicity was observed over storage periods spanning up to 80 days (longest time point evaluated). Thus, the CMC microneedle arrays and this delivery technology can enable effective cutaneous delivery of antigen and adjuvants to elicit antigen specific immunity.

To evaluate the delivery of a biologically active small molecule, pyramidal CMC-microneedle arrays were fabricated with the low molecular weight chemotherapeutic agent CYTOXAN® (cyclophosphamide), or with FLURESBRITE® (Polysciences, Inc.) green fluorescent particles as a control. CYTOXAN® (cyclophosphamide) was integrated at a concentration of 5 mg/g of CMC, enabling delivery of approximately about 140 µg per array. This is a therapeutically relevant concentration based on the area of skin targeted, yet well below levels associated with systemic toxicities. Living human skin organ cultures were used to assess the cytotoxicty of CYTOXAN® (cyclophosphamide). CYTOXAN® (cyclophosphamide) was delivered by application of arrays to skin explants as we previously described. Arrays and residual material were removed 5 minutes after application, and after 72 hours of exposure, culture living skin explants were cryo-sectioned and fixed. Apoptosis was evaluated using green fluorescent TUNEL assay (In Situ Cell Death Detection Kit, TMR Green, Roche, cat #:11-684-795-910). Fluorescent microscopic image analysis of the human skin sections revealed extensive apoptosis of epidermal cells in CYTOXAN® (cyclophosphamide) treated skin as shown in FIG. 19A. As shown in FIG. 19B, no visible apoptosis was observed in fluorescent particle treated skin though these particles were evident, validating that the observed area was accurately targeted by the microneedle array.

Direct Fabricated Microneedle Arrays

The micromilling of mastermolds described above allows the production of microneedle arrays with a variety of geometries. In another embodiment, systems and methods are provided for fabricating a microneedle array by directly micromilling various materials, such as dried CMC sheets. The same general tooling that was described above with respect to the micromilling of mastermolds can be used to directly micromilling microneedle arrays.

Direct micromilling of microneedle arrays eliminates the need for molding steps and enables a simplified, scalable, and precisely reproducible production strategy that will be compatible with large scale clinical use. Moreover, direct fabrication of the microneedle arrays through micromilling enables greater control of microneedle geometries. For example, micromilling permits the inclusion of microneedle retaining features such as undercuts and/or bevels, which cannot be achieved using molding processes.

The reproducibility of direct milling of microneedle arrays is particular beneficial. That is, in direct micromilling all of the microneedles are identical as a result of the milling fabrication process. In molding operations, it is not uncommon for some needles to be missing or broken from a given patch as a result of the process of physically separating them from the molds. For use in certain medical applications, the reproducibility of the amount of bioactive components in the array is very important to provide an appropriate level of "quality control" over the process, since irregularities in the needles from patch to patch would likely result in variability in the dose of drug/vaccine delivered. Of course, reproducibility will also be an important benefit to any application that requires FDA approval. Spincast/molded patches would require special processes to assure acceptable uniformity for consistent drug delivery. This quality control would also be likely to result in a certain percentage of the patches "failing" this release test, introducing waste into the production process. Direct micromilling eliminates or at least significantly reduces these potential problems.

Molding processes also have inherent limitations because of the need to be able to fill a well or concavity and remove the cured molded part from that well or concavity. That is because of mold geometries, undercuts must generally be avoided when molding parts or the part will not be removable from the mold. That is, a geometrical limitation of a molded part, such as a molded microneedle array, is that any feature located closer to the apex must be narrower than any feature located toward the base.

Accordingly, in view of these limitations, FIG. 20 illustrates schematic representation of microneedle shapes and structures that are generally suitable for fabrication by molding. That is, the shapes and structures shown in FIG. 20 do not contain any undercuts that would prevent the part (i.e., the microneedles) from being removed from a production mold. In contrast, FIG. 21 illustrates a beveled, undercut microneedle shape that cannot be molded in the manners described herein.

This geometry can only be created through direct fabrication using the proposed micromilling technology. The negative (bevel) angle facilitates better retention of the microneedles in the tissue. In addition, because the microneedle of FIG. 21 has a wider intermediate portion (with a larger cross-sectional dimension) above a lower portion (with a smaller cross-sectional dimension), a greater amount of the bioactive material can be delivered by configuring the microneedle to hold or store the bioactive material in the wider section, which is configured to be retained within the skin. Thus, the larger cross-sectional dimension of the intermediate portion can "carry" the bulk of the bioactive component. Since the lower portion tapers to a narrower cross-sectional dimension, the wider intermediate portion will obtain good penetration for delivery of the bioactive component into the skin layer. A portion above the intermediate portion desirably narrows to a point to facilitate entry of the microneedles into the skin layers.

Another limitation of molded parts is that it can be difficult to precisely fill a very small section of a mold. Since production molds for microneedle arrays comprise numerous very small sections, it can be difficult to accurately fill each well. This can be particularly problematic when the mold must be filled with different materials, such as a material that contains a bioactive component and a material that does not contain a bioactive component. Thus, if the production mold is to be filled with layers, it can be difficult to accurately fill the tiny wells that are associated with each microneedle. Such reproducibility is particularly important, since the microneedles are intended to deliver one or more bioactive components. Thus, even slight variations in the amounts of bioactive component used to fill production molds can be very undesirable.

Also, by using a lamination structure to form a sheet or block that can be micromilled, various active components can be integrated into a single microneedle by vertical layering. For example, in an exemplary embodiment, CMC-hydrogel and CMC-sOVA-hydrogel (80% CMC/20 wt % OVA) were layered into the form of a sheet or block. This composite sheet can be micro-machined using the direct micromilling techniques described herein.

FIG. 22 is a stereo-microscopic image analysis of an entire microneedle array. The microneedle comprises a 10×10 array of microneedles. FIG. 23 is an enlarged segment of the microneedle array of FIG. 22. The layering of two components is shown in FIG. 23, which illustrates darker areas of the microneedles at tip portions and lighter areas of the microneedles at base portions. The darker layer at the tip represents the layer comprising a bioactive component, in this case soluble ovalbumin contained in a CMC layer.

Although the formation of a layer containing active material (e.g., antigen) and the subsequent micromilling of the layer (and any other adjacent layers) may require the use of relatively large amounts of the active material, the material can be removed (e.g., in the form of chips), recovered, and recycled. Direct machining technology is not restricted by the geometrical constraints arising from the molding/demolding approach, and thus, is capable of creating more innovative needle designs (e.g., FIG. 21), which can significantly improve the retained needle-volume and needle retention time in the skin.

The production of sheets or blocks by forming a plurality of layers can provide a solid material that can be micromachined and which can comprise one or more layers with a bioactive component. For example, a dissoluble solid carboxymethylcellulose polymer based block or sheet with well-defined and controlled dimensions can be fabricated by a lamination process. The resulting sheet or block can be fully machineable, similar to the machining of plastic or metal sheets or blocks. As described herein, the fabrication process can be suitable for the incorporation of bioactive components into the matrix without significantly reducing their activity levels.

As described below, a fabricated sheet of material (such as a CMC based material) can be directly micro-machined/micromilled) to produce one or more microneedle arrays suitable for delivering active ingredients through the skin. This dissoluble biocompatible CMC block-material can be used for the delivery of soluble or insoluble and particulate agents in a time release manner for body surface application.

The biocompatible material can be suitable for implants in deeper soft or hard tissue when dissolution of the scaffolding material is required and useful.

The following method can be used to prepare a carboxymethylcellulose (CMC) polymer low viscosity hydrogel to 12.5% concentration. The 12.5% carboxymethylcellulose (CMC) low viscosity hydrogel can be prepared in water or other biocompatible buffer, such as (but not limited to) PBS or HBS. During the preparation of the polymer solution, soluble agents (such as nucleic acid, peptides, proteins, lipids or other organic and inorganic biologically active components) and particulates can be added (e.g. ovalbumin, a soluble agent). Ferrous particulates carrying active ingredients at 20 w/w % of CMC can be used.

The preparation of 1000 g sterile 12.5% CMC hydrogel with no active component can be achieved as follows:

1) Measure 125 g CMC, add 875 g water or other water based solvent.
2) Stir to homogeneity in overhead mixer.
3) Autoclave homogenate to sterility at 121 degrees Celsius for 1 hour (the autoclaving step can reduce viscosity for improved layering)
4) Cool to 22 degrees Celsius.
5) Vacuum treat the resulting material at 10 torr and 22 degrees Celsius for 1 hour to remove trapped micro-bubbles.
6) Centrifuge product at 25,000 g for 1 hour in vacuum chambered centrifuge (for floating and further removing residual micro bubbles).
7) Store the CMC-hydrogel product at 4 degrees Celsius.

The preparation of 1000 g sterile 12.5 w/w % dry content 20/80% ovalbumin/CMC hydrogel can be achieved as follows:

1) Measure 100 g CMC add 650 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5a) Dissolve 25 g ovalbumin in 225 g water.
5b) Sterile filter ovalbumin solution on 0.22 µm pore sized filter.
6) Mix to homogeneity, under sterile conditions the 750 g CMC hydrogel with 250 g sterile ovalbumin solution.
7) Vacuum treat the resulting material at 10 torr and 22 degrees Celsius for 1 hour to remove trapped micro-bubbles.
8) Centrifuge product at 25,000 g for 1 hour in vacuum chambered centrifuge (for floating and further removing residual micro bubbles).
9) Store the CMC-hydrogel product at 4 degrees Celsius.

The preparation of 100 g sterile 12.5 w/w % dry content 20/80% particulate-ovalbumin/CMC hydrogel can be achieved as follows:

1) Measure 10 g CMC add 87.5 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5) Disperse 2.5 g particulate-ovalbumin in the 97.5 g, 22 degrees Celsius CMC-hydrogel and mix to homogeneity, under sterile conditions.
6) Vacuum treat the resulting material at 10 torr and 22 degrees Celsius for 2 hour to remove trapped micro-bubbles.
7) Centrifuge product at 3,000 g for 1 hour in vacuum chambered centrifuge (for floating and further removing residual micro bubbles).
8) Store the CMC-hydrogel product at 4 degrees Celsius.

Note in this example, particulate-ovalbumin is prepared from activated iron beads reaction to ovalbumin. However, it should be noted that the above descriptions are only exemplary embodiments and other compounds and active ingredients can be used.

A solid block/sheet carboxymethylcellulose (CMC) can be fabricated in the following manner using the low viscosity CMC-hydrogels described above.

The fabrication process can comprise a laminar spreading of the polymer at a defined thickness and a drying of the layered polymer to less than about 5% water content using sterile dried air flow over the surface of the polymer layer. The above two acts can repeated until the desired block thickness is achieved.

Figure 24:
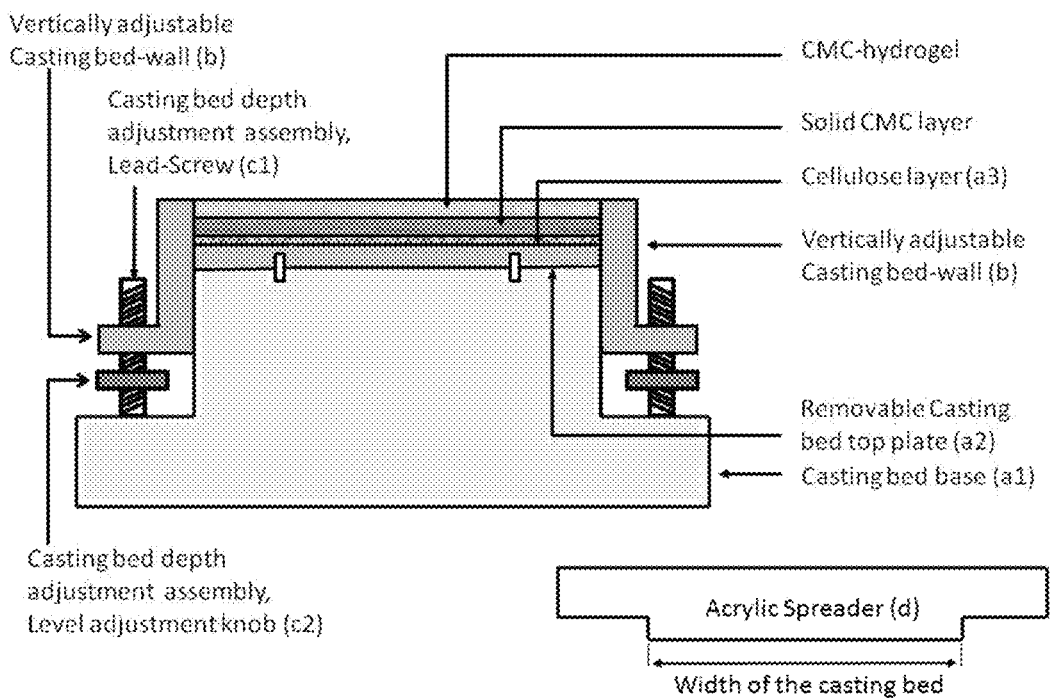
FIG. 24 is a schematic cross-sectional view of a casting-mold assembly for creating a block or sheet of material for direct micromilling.

A method of performing a laminar CMC-hydrogel layering of a defined thickness over the casting mold assembly is described with reference to FIG. 24. FIG. 24 illustrates a cross-sectional view of the casting-mold assembly which includes: (a) casting bed; (b) adjustable casting bed wall; (c) casting-bed depth adjustment assembly; and (d) an acrylic spreader. It should be noted that FIG. 24 is not drawn to scale or otherwise shown with elements in their proper proportions.

The casting mold assembly can be constructed from acrylic (Plexiglas) and can comprise a casting bed base unit, a vertically adjustable hydrophobic casting-bed wall, and a casting-bed adjustment mechanism. The casting bed base unit (a1) can include a removable/replaceable casting bed top plate (a2) with an attached cellulose layer (a3). The cellulose layer can be about 0.5 mm in thickness. The vertically adjustable hydrophobic casting-bed wall (b) can be adjusted using the casting-bed depth adjustment mechanism, which can be comprised of lead-screw (c1) and level adjustment knob (c2). In the illustrated embodiment, a quarter turn of this knob can result in a 0.5 mm lift of the bed wall.

Initially, the adjustable casting bed wall can be set to height where the distance between the acrylic spreader and the cellulose layer of the bed is about 1 mm when the spreader is in position. A predefined volume (e.g., about 0.1 ml/cm2) of the 12.5% CMC-hydrogel can be added and layered. The layer can be evened or leveled by sliding the acrylic spreader (d) on the top surface of the adjustable casting wall to yield an even layer of about 1 mm of CMC-hydrogel. The layered CMC-hydrogel can be dried to a solid phase in the drying apparatus shown in FIG. 25 and described in more detail below.

The layering and drying steps can be repeated until the desired layered structure (sheet) is achieved. The casting bed wall can be raised by an appropriate amount during the addition of each layer. For example, after adding each layer, the bed wall can be raised or lifted by about 0.5 mm. Thus, the above-described cycle can deposit about 0.5 mm solid CMC layer. The process (e.g., the layering of material, the raising of bed wall, etc.) can be repeated until the desired block thickness achieved.

Figure 25:
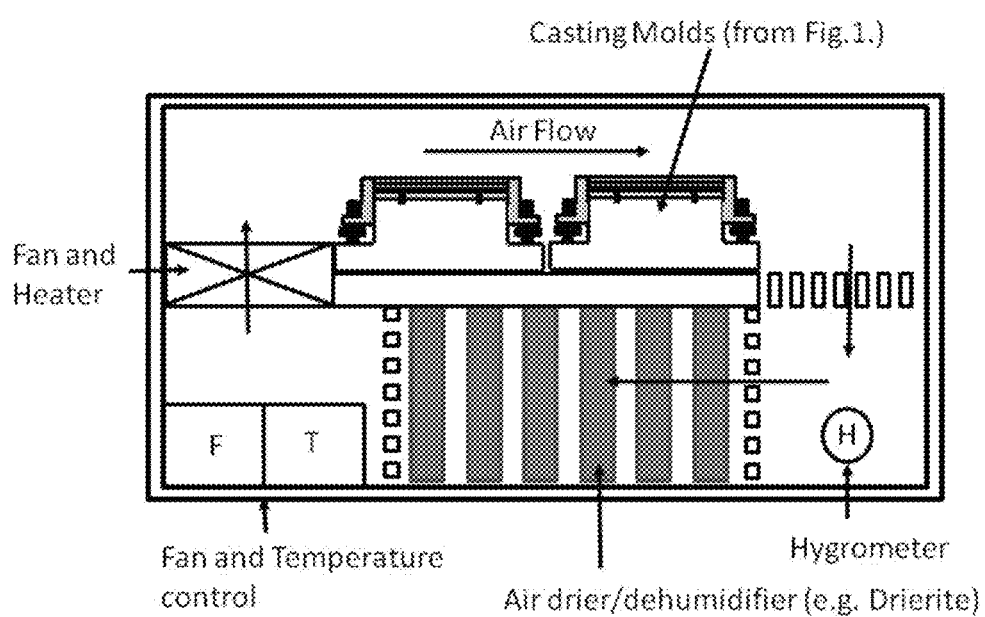
FIG. 25 is a schematic cross-sectional view of a drying apparatus that can be used to dry a block or sheet of material for direct micromilling.

The layered CMC-hydrogel polymer can be dried in various manners. For example, FIG. 25 illustrates a drying apparatus that can be used to dry the various deposited layers of the sheet material. It should be noted that FIG. 25 is not drawn to scale or otherwise shown with elements in their proper proportions. A fan can provide continuous gas flow (e.g., air or other inert gas, such as nitrogen) over the CMC-hydrogel layered in the casting mold assembly. The gas flow will result in a gentle dehydration of the CMC-hydrogel layer. The drying speed can be adjusted to prevent or reduce gas enclosures (e.g., air bubbles) in the solid CMC product. The humid air over the layer can be dried over desiccant (e.g., an air dryer or dehumidifier), temperature adjusted, and returned over the hydrogel again by the speed-controlled fan. A hygrometer can be positioned on the humid side of the chamber to provide an indication of the status of the drying process. After a predetermined dryness has been achieved, as indicated by the hygrometer, the drying process can be ended.

Airflow can be adjusted to affect the drying speed. In the exemplary embodiment, the airflow is controlled to be between about 0.1-2.0 m/sec; the temperature is between ambient and about 50 degrees Celsius. Using these configurations, the drying time of a single layer CMC-hydrogel can be about 0.5-4 hours depend on the airflow and the set temperature.

The pure CMC based product can be transparent, light off white, or amber colored. Its specific gravity can be about 1.55-1.58 g/ml. The product is desirably free of microbubbles and otherwise suitable for fabricating micron scale objects. The physical characterization of the final block/sheet product (hardness, tensile strength, etc.) can vary, but should generally be able to resist physical stresses associated with micromilling.

As described above, the microneedle arrays disclosed herein are capable of providing reliable and accurate delivery methods for various bioactive components. The structural, manufacturing, and distribution advantages characteristic of the above-described microneedle arrays can be particularly applicable for use in delivering vaccines. Advantages of these microneedle arrays include (1) safety, obviating the use of needles or living vectors for vaccine delivery, (2) economy, due to inexpensive production, product stability, and ease of distribution, and 3) diversity, via a delivery platform compatible with diverse antigen and adjuvant formulations.

Moreover, cutaneous immunization by microneedle array has important advantages in immunogenicity. The skin is rich in readily accessible dendritic cells (DCs), and has long been regarded as a highly immunogenic target for vaccine delivery. These dendritic cell populations constitute the most powerful antigen presenting cells (APCs) identified thus far. For example, genetic immunization of skin results in transfection of dendritic cells in murine and human skin, and these transfected dendritic cells synthesize transgenic antigens, migrate to skin draining lymph nodes, and efficiently present them through the MHC class I restricted pathway to stimulate CD8+ T-cells. The immune responses induced by skin derived DCs are remarkably potent and long-lasting compared to those induced by other immunization approaches. Recent clinical studies demonstrate that even conventional vaccines are significantly more potent when delivered intradermally, rather than by standard intramuscular needle injection. Thus, microneedle arrays can efficiently and simultaneously deliver both antigens and adjuvants, enabling both the targeting of DCs and adjuvant engineering of the immune response using the same delivery platform.

In view of the many possible embodiments to which the principles of the disclosed embodiments may be applied, it should be recognized that the illustrated embodiments are only preferred examples and should not be taken as limiting the scope of protection. Rather, the scope of the protection is defined by the following claims. We therefore claim all that comes within the scope and spirit of these claims.

We claim:

1. A dissolvable microneedle array formed from a sheet of material having a plurality of layers, at least one of the plurality of layers comprising a bioactive component;
   the sheet of material being micromilled to form a microneedle array, the microneedle array comprising a base portion and plurality of microneedles extending from the base portion,
   wherein each microneedle comprises a plurality of layers of a dissoluble biocompatible material and the dissoluble biocompatible material comprises carboxymethylcellulose.

2. A dissolvable microneedle array comprising:
   a base portion; and
   a plurality of microneedles, the microneedles extending from a surface of the base portion and being pre-formed to have a pillar-shape,
   wherein the microneedles comprise carboxymethylcellulose.

3. The dissolvable microneedle array of claim 2, wherein respective microneedles further comprise a fillet portion, the fillet portion being located at the area where respective microneedles contact the base portion.

4. The dissolvable microneedle array of claim 2, wherein each microneedle comprises a plurality of layers of dissoluble biocompatible material.

5. The dissolvable microneedle array of claim 2, wherein the bioactive component comprises a chemotherapeutic agent.

6. The dissolvable microneedle array of claim 2, wherein at least the top portion comprises a dye.

7. The dissolvable microneedle array of claim 2, wherein the dissolvable microneedle array is configured for delivery of biologically active molecules to human skin wherein the delivery of biologically active molecules to human skin comprises penetrating the stratum corneum to deliver the biologically active molecules to the epidermis and/or dermis.

8. The dissolvable microneedle array of claim 2, wherein the dissolvable microneedle array is configured for insertion into the dermis of a patient.

9. The dissolvable microneedle array of claim 2, wherein the pillar type microneedle comprises a base portion, which is generally polygonal in cross section, and a projecting portion that extends from the base portion.

10. The dissolvable microneedle array of claim 2, wherein the projecting portion has a lower portion that is substantially rectangular and tip portion that generally tapers to a point.

11. The dissolvable microneedle array of claim 2, wherein the tip portion is generally pyramidal in shape.

12. The dissolvable microneedle array of claim 2 the exposed faces of the pyramid can be either flat or arcuate.

13. The dissolvable microneedle array of claim 2, wherein the projecting portion can be half or more the entire length of the needle.

* * * * *

UNITED STATES PATENT AND TRADEMARK OFFICE
CERTIFICATE OF CORRECTION

PATENT NO. : 11,744,927 B2
APPLICATION NO. : 16/861112
DATED : September 5, 2023
INVENTOR(S) : Falo, Jr. et al.

It is certified that error appears in the above-identified patent and that said Letters Patent is hereby corrected as shown below:

In the Claims

Column 21, Lines 7-8, Claim 12 "The dissolvable microneedle array of claim 2 the exposed faces of the pyramid can be either flat or arcuate" should read -- The dissolvable microneedle array of claim 2, wherein the exposed faces of the pyramid can be either flat or arcuate --

Signed and Sealed this
Fifth Day of December, 2023

Katherine Kelly Vidal
*Director of the United States Patent and Trademark Office*